(12) United States Patent
Davidowitz et al.

(10) Patent No.: US 8,346,382 B2
(45) Date of Patent: Jan. 1, 2013

(54) HIERARCHICAL SAMPLE STORAGE SYSTEM

(75) Inventors: Hananel Davidowitz, Princeton, NJ (US); Thomas Coradetti, Princeton, NJ (US); Yair Talmi, Hamilton, NJ (US)

(73) Assignee: ColdTrack, LLC, Princeton, NJ (US)

( * ) Notice: Subject to any disclaimer, the term of this patent is extended or adjusted under 35 U.S.C. 154(b) by 1004 days.

(21) Appl. No.: 12/064,748

(22) PCT Filed: Aug. 14, 2006

(86) PCT No.: PCT/US2006/031668
§ 371 (c)(1),
(2), (4) Date: Jul. 17, 2008

(87) PCT Pub. No.: WO2007/024540
PCT Pub. Date: Mar. 1, 2007

(65) Prior Publication Data
US 2009/0026907 A1    Jan. 29, 2009

Related U.S. Application Data

(66) Substitute for application No. 60/712,016, filed on Aug. 26, 2005.

(60) Provisional application No. 60/906,778, filed on Mar. 12, 2007, provisional application No. 60/771,582, filed on Feb. 8, 2006.

(51) Int. Cl.
*G06F 19/00* (2011.01)
(52) U.S. Cl. .......................... 700/125; 700/124; 422/105
(58) Field of Classification Search .................. 700/214, 700/215, 225, 236, 242, 241; 422/105
See application file for complete search history.

(56) References Cited

U.S. PATENT DOCUMENTS

| | | | |
|---|---|---|---|
| 5,565,858 A | 10/1996 | Guthrie | 340/825.35 |
| 6,405,102 B1 | 6/2002 | Swartz et al. | 700/225 |
| 7,091,864 B2 | 8/2006 | Veitch et al. | |
| 2002/0023441 A1 | 2/2002 | Bara et al. | 62/125 |
| 2005/0060062 A1* | 3/2005 | Walker et al. | 700/236 |
| 2005/0069861 A1 | 3/2005 | Zimmermann et al. | 435/1.1 |
| 2006/0102645 A1 | 5/2006 | Walker et al. | |

FOREIGN PATENT DOCUMENTS

DE    201 21 738 U 1    9/2003
WO    WO 2004/102330 A2    11/2004

* cited by examiner

*Primary Examiner* — Natalia Levkovich
(74) *Attorney, Agent, or Firm* — Mendelsohn, Drucker & Associates, P.C.; Steve Mendelsohn

(57) ABSTRACT

In one embodiment, a cold storage system for biological samples has one or more freezers, each freezer having one or racks, each rack receiving one or more boxes, each box receiving one or more sample containers. In addition to the biological sample, each sample container has a unique passive RFID tag. Control electronics in each box energize reader coils to query individual RFID tags. Control electronics in each rack communicate with and provide power to the control electronics of each corresponding box, and control electronics in each freezer communicate with and provide power to the control electronics of each corresponding rack, and a host computer communicates with the control electronics in each freezer. In each instance, communication and power provisioning is implemented using magnetic inductive coupling. The system is able to determine the identity of each sample container in the system and maintain that information in a database.

31 Claims, 18 Drawing Sheets

FIG. 15A

```
         1502      1506                1508
          |         |                    |
         SA:E7A6477740C1:05:05:04:C:09:07573307312E97D6A2D69ECCD
                     1504
                   1510  1512 1514 1516 1518
```

```
                             ...
00419:DO:9A2158749F64:2008:12:26:14:27:06:C6774A179B0197827248OB8D
00420:DC:9A2158749F64:2008:12:26:14:32:57
00421:IT:9A2158749F64:01:01:A:01:604D51E34376D9C4255CA1EC
00422:SA:9A2158749F64:01:01:A:02:39C9C80DF9A2CC05754774D5
00423:SA:9A2158749F64:01:01:A:03:FF3397F8034C4803FC6580DB
00424:SA:9A2158749F64:01:01:A:04:B5DB870F6E37AA25FB85F7A4
00425:SA:9A2158749F64:01:01:A:05:6A32A5583B8F7F8B9DC6D961
00426:SA:9A2158749F64:01:01:A:06:F2F9BA026FABF403B6DD22E7
00427:SA:9A2158749F64:01:01:A:07:BBA0DCB62B10627A638748C9
00428:SA:9A2158749F64:01:01:A:08:0A42DC997B30953B22AF5043
00429:SA:9A2158749F64:01:01:A:09:909101F7CD0E5AED3F7E0CAE
00430:SA:9A2158749F64:01:01:A:10:E154D74C1D559FE134F094A7
00431:SA:9A2158749F64:01:01:B:01:9FBF7B9BB9BF4BB5B8988C7A
00432:SA:9A2158749F64:01:01:B:02:131E3943AC0B4B305DE88DED
00433:SA:9A2158749F64:01:01:B:03:3C17E87BC54A588CBB12CF4D
00434:SA:9A2158749F64:01:01:B:04:D936AAA071D8929ODA3DF92FE
00435:SA:9A2158749F64:01:01:B:05:2869CCBD5399823777E6FEBB8
00436:SA:9A2158749F64:01:01:B:06:9A71EF30E62129514FCD6103
00437:SA:9A2158749F64:01:01:B:07:A2AD22775A4D8DB0C7D550F00
00438:SA:9A2158749F64:01:01:B:08:C842CB89FA0943BA9EDF92B6
00439:SA:9A2158749F64:01:01:B:09:509O1C7722AE32BE5E7AC74D0
00440:SA:9A2158749F64:01:01:B:10:728D9BBF6AA453A454A13B6A99A
00441:SA:9A2158749F64:01:01:                             ...
```
FIG. 15B

```
                            ...
00001:IR:C57424343D91:2008:12:26:14:32:57
00002:SA:C57424343D91:01:03:14:B:07:628BA173B543C404CAD861A0
00003:SA:C57424343D91:04:04:07:D:10:74CDBEE163377147AF3FF15
00004:SA:C57424343D91:03:08:05:I:01:577DE7446CBEC41A5FEB188F
00005:SA:C57424343D91:03:05:10:A:06:9A00621E8225A640388D954AD
00006:SA:C57424343D91:03:04:15:I:01:192E3FB0C3CA6582A251BFB
00007:SA:C57424343D91:05:08:03:D:07:6031B0000957BDD0B9D9E4E03
00008:SA:C57424343D91:02:02:14:C:09:C04B8DA3B5B4685C76F953E7
00009:SA:C57424343D91:01:02:06:I:07:5239680CC35C48C76E514486
00010:SA:C57424343D91:03:08:19:F:07:B821AE42E511061F27936492
00011:SA:C57424343D91:04:01:09:E:01:10A8B144344SEC886704DF1A
00012:SA:C57424343D91:04:03:08:B:02:59CE2A76F32F5601DFC17617
00013:SA:C57424343D91:05:04:10:B:09:ACAFCBA2597AD5CD05A43F86
                            ...
```
FIG. 15C

```
                         ...
06179:SA:E529E9886A7C:06:01:13:I:03:106A5088618C435DB0319F31
06180:SA:E529E9886A7C:01:04:09:D:09:6BA9A844504B48AA410277CC
06181:SA:E529E9886A7C:01:02:05:A:08:01F4675A08C69C654C363FFA
06182:DO:E529E9886A7C:2008:12:26:14:27:06:6B788E5114C3FBAF822C575
06183:DC:E529E9886A7C:2008:12:26:14:32:57
06184:SA:E529E9886A7C:04:03:03:F:02:B22909BEEA143AA9CED3EEFBB
06185:SA:E529E9886A7C:06:07:17:G:08:B04C40F27560S229A3974E1D
06186:SA:E529E9886A7C:04:07:02:F:05:E77F0EAFE8F9A153B234DC7C
                         ...
```
FIG. 15D

HIERARCHICAL SAMPLE STORAGE SYSTEM

CROSS-REFERENCE TO RELATED APPLICATIONS

This application claims the benefit of the filing date of PCT application no. PCT/US06/31668 filed on Aug. 14, 2006, which in turn claimed the benefit of the filing dates of U.S. provisional application Nos. 60/712,016 filed on Aug. 25, 2005, and 60/771,582 filed on Feb. 8, 2006, the teachings of both of which are incorporated herein by reference. This application also claims the benefit of the filing date of U.S. provisional application No. 60/906,778 filed on Mar. 12, 2007, the teachings of which are incorporated herein by reference.

BACKGROUND OF THE INVENTION

1. Field of the Invention

The present invention relates to the storage of samples, such as the cold storage of biological samples in freezers.

2. Description of the Related Art

Biological samples are collected and stored in many different types of facilities, for a great variety of applications. Such applications include the storage of samples collected during clinical trials in pharmaceutical companies, research samples used in university labs, samples archived in hospitals, samples used in the discovery of biological markers for diagnostic testing, forensic samples from crime or disaster scenes, samples at the Center for Disease Control (CDC), samples for various genetic studies, and so on.

As a result, cold storage systems for biological samples are ubiquitous. Typically, in these systems, each of a large numbers of samples is stored in its own small plastic tube. Tracking of the samples is done by reading handwritten labels or bar codes on the tubes or boxes that hold the tubes. Problems are many, including: poor writing surfaces, little room for extensive information, ice-impaired reading by humans or optical scanners, difficulty locating a particular sample among up to 20,000 or more samples in a typical freezer, loss of records or memory containing information on arrangements of collections, personnel turnover, accidental mixing or spilling of collections, and the inevitable confusion when reorganizing collections for new projects. Addressing these issues is becoming more important as the demands on sample tracking increase.

SUMMARY OF THE INVENTION

In one embodiment, the present invention is a system for storing samples, the system comprising one or more (e.g., uniquely identifiable) cabinets, each cabinet comprising cabinet control electronics and one or more hierarchy levels, each hierarchy level comprising control electronics adapted to communicate with control electronics of one or more elements of a next-lower hierarchy level. A lowest hierarchy level in each cabinet is a box level comprising one or more boxes for each element of a second-lowest hierarchy level in each cabinet. Each box at the box level comprises box control electronics and adapted to receive one or more corresponding sample containers, each sample container comprising container electronics and adapted to store a sample. The cabinet control electronics of each cabinet is adapted to communicate with control electronics of each element of a highest hierarchy level in each cabinet. The box control electronics of each box are adapted to communicate with the container electronics of each corresponding sample container. The container electronics of each sample container is adapted to communicate sample-identification information to the corresponding box control electronics. The corresponding box control electronics is adapted to communicate the sample-identification information to control electronics of the corresponding element of the second-lowest hierarchy level. Control electronics of each element of a second-highest hierarchy level is adapted to communicate the sample-identification information to the corresponding cabinet control electronics.

The number of hierarchy levels may be different in different implementations of the proposed system, but, in preferred implementations, each sample will have associated with it an address that can describe, up to the level of detail required, its location, when it was removed from the freezer, and by whom.

Depending on specific implementations, the technology can provide some, or all, of the following advantages: a) it will reduce the loss of samples due to lost or illegible labeling, b) it will establish a provenance for each sample including who accessed the sample and when, c) it will allow easy recovery from spills and misplaced samples, and d) it will increase the "institutional memory" of stored samples—independent of personnel and written records.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2 shows a top view of a box (with cover removed) that can be used as a box in FIG. 1, while

FIGS. 15A-D shows a possible addressing and database scheme for samples.

DETAILED DESCRIPTION

Figure 1:
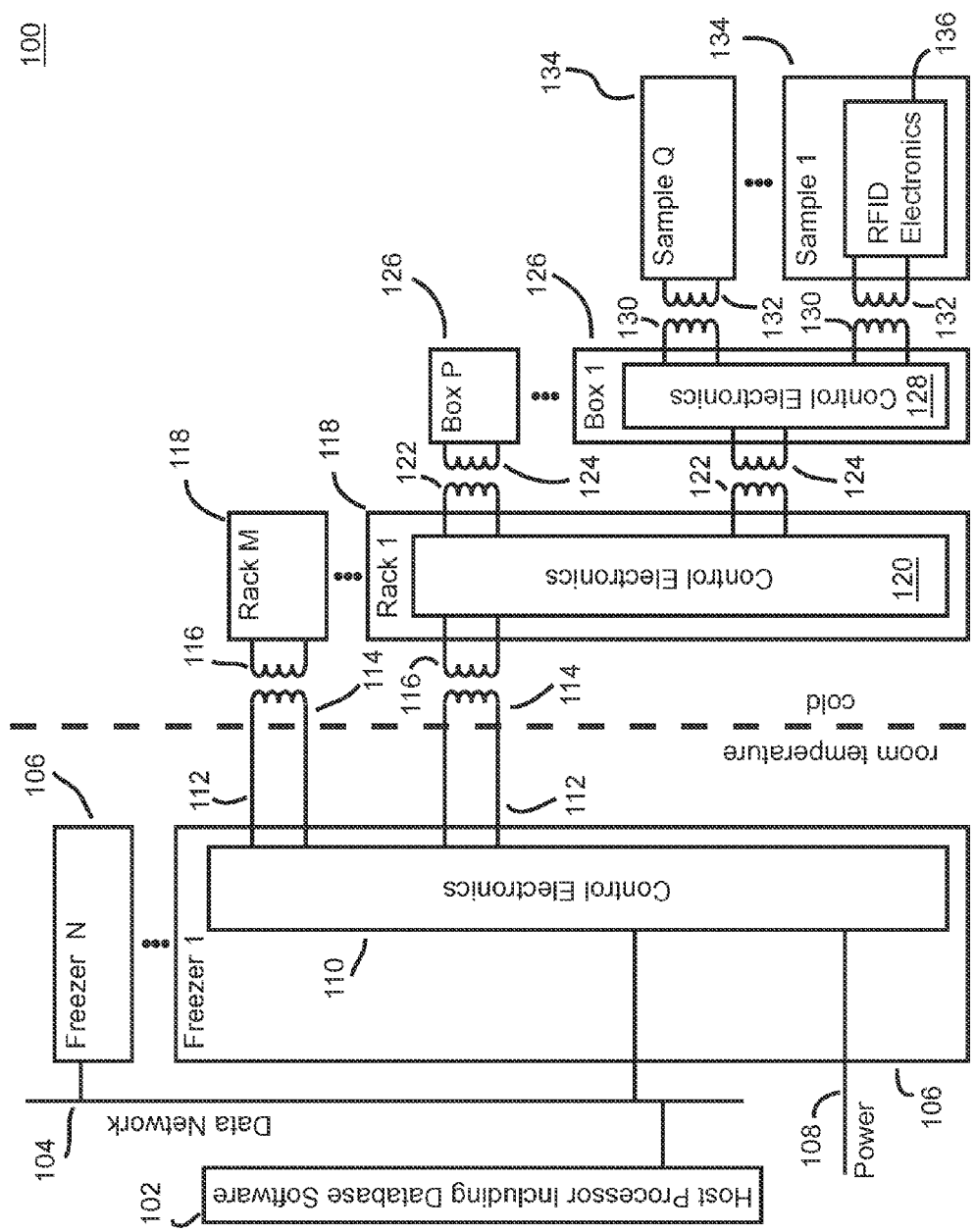
FIG. 1 shows a block diagram of a cold storage system according to one embodiment of the present invention.

FIG. 1 shows a block diagram of cold storage system 100, according to one embodiment of the present invention. Cold storage system 100 includes (remote or local) host computer 102 in communication with one or more freezers 106 via a suitable, preferably secure data network 104 (e.g., based on a standard interface, such as, BlueTooth, USB 2.0, IEEE 802.3 (Ethernet), or a wireless technology, such as, but not limited to 802.11 in its various forms). Each freezer 106 has freezer control electronics 110 and one or more racks 118. Each rack 118 has rack control electronics 120 and can support one or more boxes 126. Each box 126, in turn, has box control electronics 128 and locations (i.e., slots) for receiving one or more sample containers 134, each of which has radio frequency identification (RFID) tag electronics 136 and a biological sample (not shown), where the RFID tag is physically separated from the biological sample. Biological samples may be of any type, including but not restricted to buccal swabs, urine, blood, plasma, serum, semen, stool, biopsy, and tissue.

Within each instance of system 100 (and possibly for multiple instances of system 100), each freezer 106 has a unique freezer ID number. For each freezer 106 (and possibly for multiple instances of freezer 106), each rack 118 has its own unique rack ID number. For each rack 118 (and possibly for multiple instances of rack 118), each box 126 has its own unique box ID number. For each box 126 (and possibly for multiple instances of box 126), each slot has its own unique slot ID number (e.g., row and column address). For system 100 (and possibly for multiple instances of system 100), each RFID tag has its own unique tag ID number. Based on this ID number scheme, each sample container 134 is stored in system 100 in a location having a system-unique location identifier consisting of one or all of its corresponding freezer ID number, rack ID number, box ID number, and slot ID number. Host computer 102 maintains a database that correlates each sample container's unique tag ID number with its unique location identifier.

In a preferred implementation, RFID tag 136 is based on a conventional RFID tag, such as the LRI64 Memory TAG IC from ST Microelectronics of Geneva, Switzerland, which is a 64-bit, 13.56-MHz, unique-ID RFID tag that is compliant with both ISO 15693 and ISO18000-3 Mode 1 standards. The LRI64 Memory TAG IC is a (2 mm×3 mm) device having two active pins that connect to an external tag antenna coil. A nearby reader coil transmits a carrier signal at 13.56 MHz, where the reader and tag coils form the primary and secondary windings of a transformer, such that power from the reader is coupled through this transformer to the tag, which uses the load modulation method to transmit its ID number by selectively changing how much of a load it presents to the tag antenna. The reader senses this transformer load change, obtaining information from the tag. The reader can also modulate a carrier signal, to convey information to the tag. Each LRI64 tag has a unique 64-bit ID determined by the manufacturer. The LRI64 tag also has a small amount of write-once data storage available to be controlled by cold storage system 100. As a passive device, the LRI64 tag only responds to requests, which can be specific to one tag, all tags, or some but not all tags. Of course, other RFID tags having other operating characteristics may be used in other implementations of the present invention.

Referring again to FIG. 1, box control electronics 128 is a printed circuit board (PCB) having (at least one) reader coil 130 corresponding to each slot in box 126 that can receive a sample container 134. In one implementation, for each slot in box 126 that can receive a sample container 134, box control electronics 128 has a single reader coil 130 positioned under that slot, so that tag coil 132 within the corresponding sample container 134 is sufficiently close to that corresponding reader coil 130 to enable RF communication between the two coils.

Figure 2:
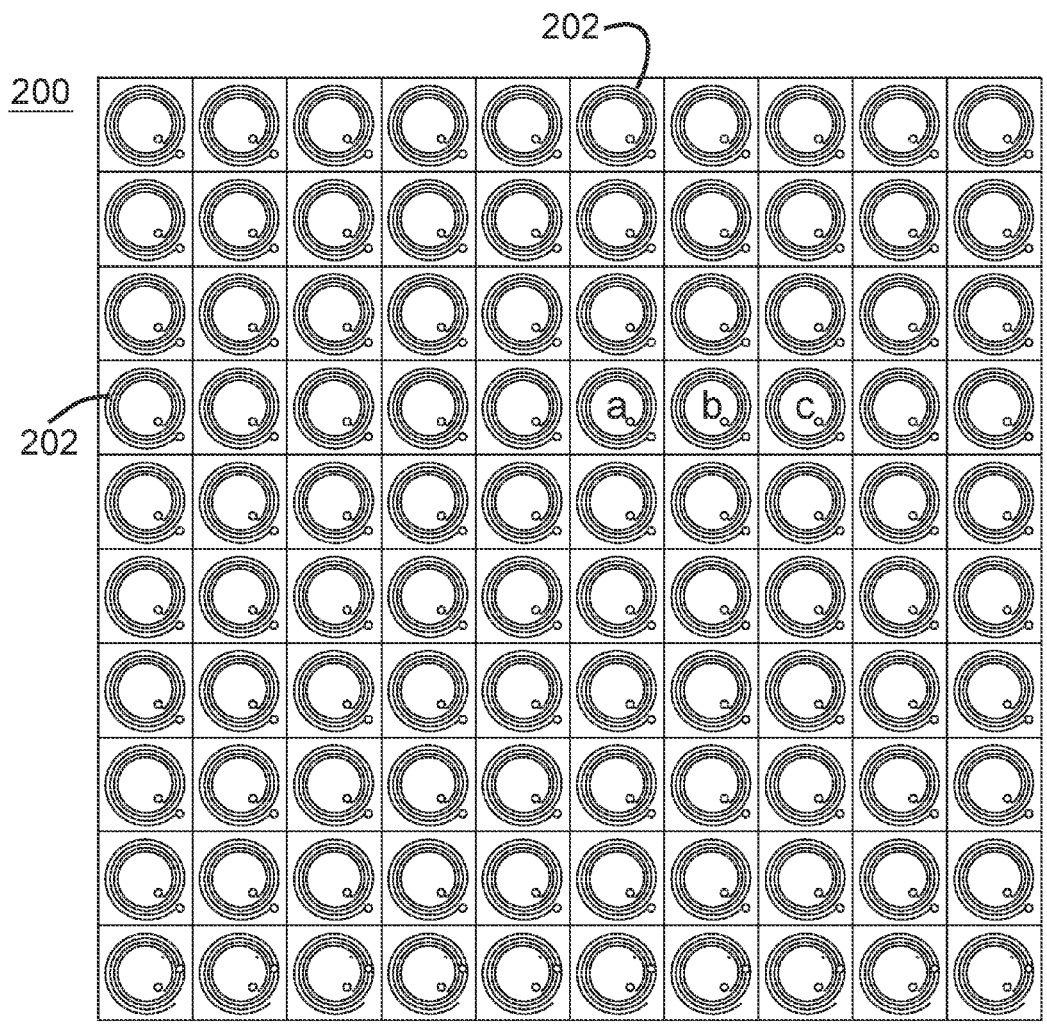
Figure 3:
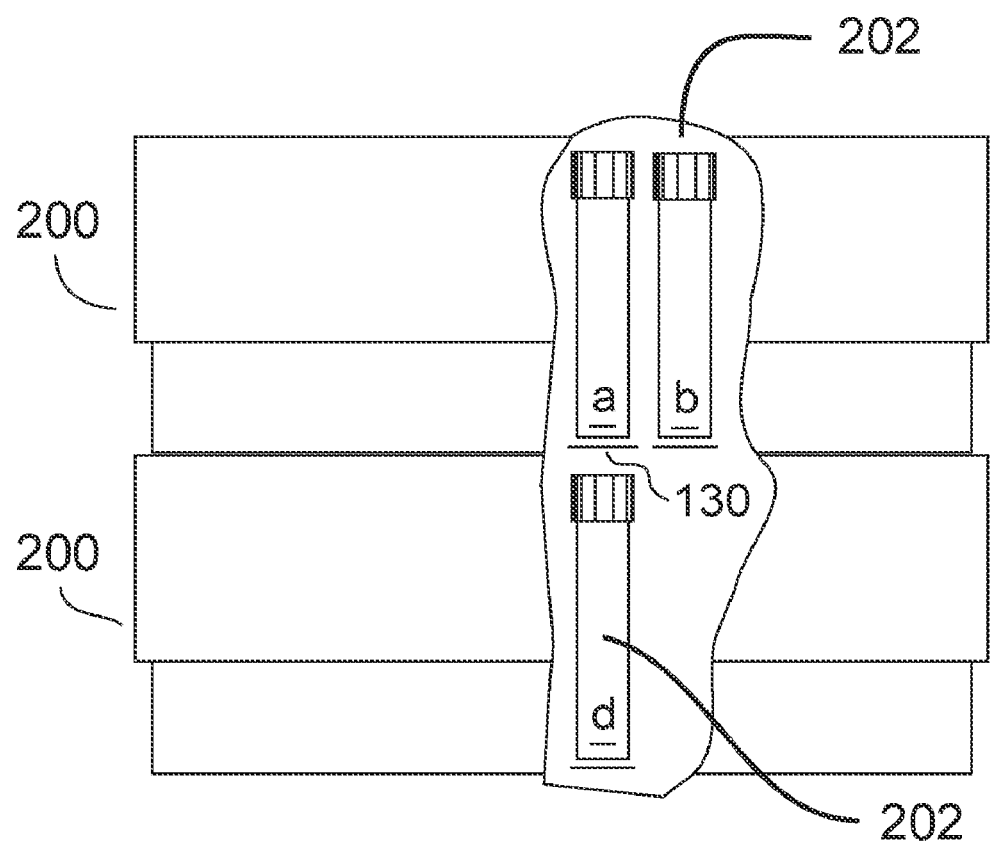
FIG. 3 shows a partial cutaway side view of two such boxes, one stacked upon the other.

FIG. 2 shows a top view of a box 200 (with cover removed) that can be used as a box 126 in FIG. 1, while FIG. 3 shows a partial cutaway side view of two such boxes 200, one stacked upon the other. As shown in FIG. 2, box 200 has a (10×10) array of slots 202, each of which can receive and hold a different sample container 134. In this implementation, box control electronics 128 has a corresponding (10×10) array of reader coils 130 aligned with and just below the (10×10) array of slots 202.

Referring again to FIG. 1, in addition to being able to communicate with RFID tag 136 of each received sample container 134 via reader coils 130 and tag coils 132, box control electronics 128 of each box 126 is capable of communicating with rack control electronics 120 of the corresponding rack 118 via upstream box coil 124 and corresponding downstream rack coil 122. Similarly, rack control electronics 120 of each rack 118 is capable of communicating with freezer control electronics 110 of the corresponding freezer 106 via upstream rack coil 116 and corresponding downstream freezer coil 114. In addition to supporting upstream and downstream data communications, the transformer formed by each corresponding pair of coils 114/116 inductively transfers operating power (provided by, e.g., 50-60 Hz, 120-240 VAC power supply 108) from each freezer 106 to each corresponding rack 118, and the transformer formed by each corresponding pair of coils 122/124 inductively transfers operating power from each rack 118 to each corresponding box 126 supported by that rack.

As represented in FIG. 1, during normal operations, the equipment upstream of freezer coils 114 (i.e., the left side of FIG. 1) operates at ambient (e.g., room) temperature, while freezer coils 114 and the equipment downstream of freezer coils 114 (i.e., the right side of FIG. 1) operate at the cold temperatures used to store the biological samples. Although temperatures may vary from application to application, biological samples are typically stored at temperatures of about −80C or lower (e.g., near the boiling point of liquid nitrogen). Obviously, the electronics within the cold side of the freezers needs to function properly at the applicable cold temperature levels. Such electronics also preferably operates satisfactorily at higher (e.g., room) temperature ranges, to maintain operations even when the freezers are not cold.

In order to avoid overloading the cooling systems of the freezers, it is desirable to minimize the transfer of heat from the warm (i.e., room-temperature) side to the cold side via the electrical connections 112 between freezer control electronics 110 and freezer coils 114. One way to reduce such thermal loading is to implement electrical connections 112 using stainless steel, copper-coated stainless steel, or some other alloy or configuration that has relatively low thermal conductivity compared to copper. Alternatively or in addition, relatively long conductors can be used to implement electrical connections 112 including those with diagonal configurations or serpentine shapes to reduce heat transfer.

Figure 4:
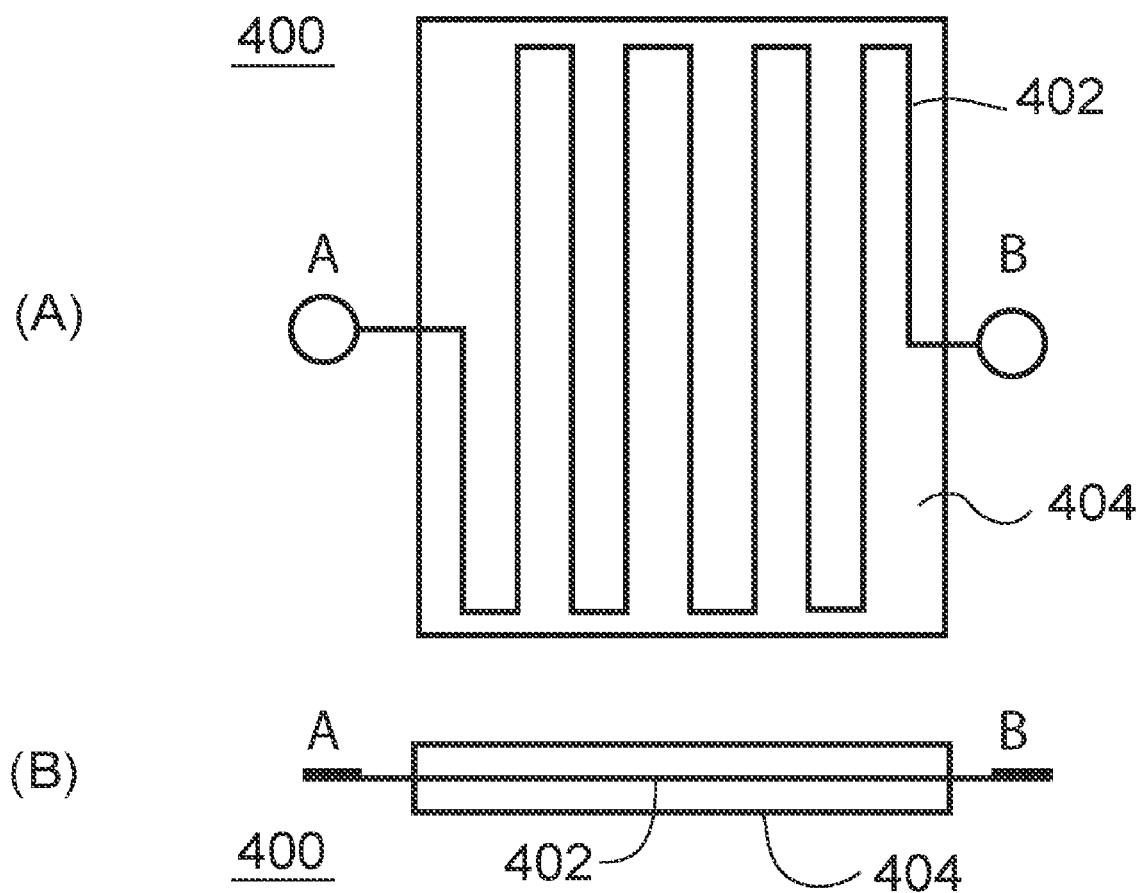
FIGS. 4A and 4B show cross-sectional top and side views of a schematic representation of a serpentine electrical connection that can be used for each electrical connection 112 of FIG. 1.

FIGS. 4A and 4B show cross-sectional top and side views of a schematic representation of an electrical connection 400 between pads A and B and having a serpentine metal trace 402 embedded within thermal-insulation material 404 that can be used for each electrical connection 112 of FIG. 1. The shape of the serpentine path will be determined by the details of the thermal gradients in the system and will be optimized to minimize the thermal load on the freezer.

Referring again to FIGS. 2 and 3, in order to communicate with RFID tag "a," the reader coil 130 directly below tag "a" is appropriately energized (by the corresponding box control electronics 128 of FIG. 1) to communicate with tag "a" via the corresponding tag coil 132. In addition to activating tag "a," it is possible that the RFID tags of one or more nearby containers (e.g., tag "b" of FIG. 2 and/or tag "d" of FIG. 3) might also get activated by the energy emitted by the reader coil directly below tag "a."

In a preferred implementation, the operating characteristics and physical construction and layout the various elements of cold storage system 100 (e.g., the reader and tag coils, the RFID tag, the boxes, and the sample containers) are designed and/or selected such that successful communications are supported only between corresponding reader/tag coil pairs. Alternatively, RFID technology that supports collision recovery processing can be used to handle situations in which more that one RFID tag is activated simultaneously in response to the energizing of an individual reader coil.

Using a 13.56-MHz carrier frequency to energize the reader coil associated with tag "a," the resulting magnetic field strength at tag "b" was estimated (using a spherical harmonic expansion of the field using Legendre polynomials and associated Legendre functions) to be smaller by a factor of $7.4 \times 10^{-5}$ than the magnetic field strength at tag "a," for a 10-mm separation (typical of a sample box) between tags "a" and "b." For a 42-mm separation (typical of a sample box) between tags "a" and "d," the magnetic field strength at tag "d" was estimated to be 2.6×10-times smaller than the magnetic field strength at tag "a." These results are consistent with the principle that field strength from a magnetic dipole (where the reader coil is a magnetic dipole) is inversely proportional to the cube of the distance from the dipole.

In a system employing passive RFID tags that (1) derive their power from downstream queries and (2) transmit messages upstream only in response to such downstream queries, a successful communication involves sufficiently energizing a reader coil to drive a tag coil to activate its tag electronics such that the tag electronics in turn sufficiently energizes that tag coil such that the corresponding box control electronics can detect changes at the original reader coil. Given the estimated relative magnetic field strengths at tags "a," "b," and "d" in the previous example, cold storage system 100 can be designed such that the likelihood of inadvertently activating tags at positions "b", "c", "d", and all other positions other than position "a" by energizing the reader coil at position "a" is exceedingly small. Even if the wrong tag were activated, symmetry arguments imply that the resulting upstream signal from the wrong tag would be attenuated by a similar factor, thereby making the possibility of successful communication between a reader coil and a wrong tag (or even significant interference to desired communication between the reader coil and the correct tag) substantially negligible.

A sinusoidal carrier-signal current variation in a reader coil induces a voltage in the adjacent tag coil via magnetic coupling, where the peak tag coil voltage should be sufficient to power the tag electronics after rectification. Based on a relatively simple model of the magnetic coupling between two parallel coils on the same axis, the proportionality of the peak voltage VT at the tag coil is given by formula (I) as follows:

$$v_T \propto \frac{f_c n_T n_R (r_T r_R)^2}{(r_R^2 + d_{RT}^2)^{3/2}}, \quad (1)$$

where:
 $f_c$ is the carrier frequency of the signal used to energize the reader coil;
 $n_T$ is the number of tag coil turns;
 $n_R$ is the number of reader coil turns;
 $r_T$ is the tag coil radius;
 $r_R$ is the reader coil radius; and
 $d_{RT}$ is the distance between the reader coil and the tag coil.
For a design goal of small, densely packed sample containers, the coil radii $r_T$ and $r_R$ and the intercoil distance $d_{RT}$ are driven toward small values. To simplify manufacturing and reduce costs, coils with small numbers of turns $n_T$ and $n_R$ are desirable. If the number of tag coil turns is small enough, then the tag coil could possibly be (but does not have to be) implemented on the tag chip itself. In one implementation, the reader coils are formed of either wound wires or conducting metal integrated into the traces at different levels of the printed circuit board used to implement box control electronics 128. The choice of carrier frequency $f_c$ may be driven towards commonly used standard values of commercially available RFID devices. For example, one possible implementation involves a carrier frequency of 13.56 MHz (corresponding to the ISO 15693 RFID standard) and the following set of reasonable parameters: $n_T=2$, $r_T=4$ mm, $n_R=50$, $r_R=4$ mm, and $d_{RT}=2$ mm. The use of lower standard carrier frequencies is less desirable because the number of turns in the reader coil and/or the tag coil could become prohibitively large. Of course, other implementations can be based on other sets of parameter values including other carrier frequencies, including LF (e.g., up to 100 s of kHz), HF (e.g., near 10 to 20 MHz), or UHF (e.g., 100 s to MHz to several GHz) frequencies.

In addition to each sample container 134 having is own RFID tag 136, each box 126 may also have its own identification (ID) chip, such as a 1-Wire® chip from Dallas Semiconductor Corp. of Dallas, Tex., integrated within or separate from box control electronics 128. In this case, each rack 118 will query the ID chip of each box 126, where host computer 102 maintains a database that correlates individual boxes 126 with specific rack locations. Such a database can be used to keep track of the individual characteristics of each box 126, such as the size of the array of slots and the types of sample containers that can be stored in the box. In a similar manner, each rack 118 and/or each freezer 106 may have its own ID chip at the freezer and/or system levels, respectively, to identify and track each rack and/or each freezer.

In another embodiment of the present invention (not shown), box electronics 128 is integrated not with each box 126, but with the corresponding rack 118, such that box electronics 128 remains in the rack, when box 126 containing sample containers 134 is removed from the rack. In this case, box 126 has affixed to it one or more additional RFID tags 136, called box tags, and box electronics 128 includes additional reader coils 130 for reading the box tags rather than sample tags. This can be accomplished with no additional electronics using anticollision techniques as well. If a box tag is appropriately placed, e.g., mounted in a reserved sample location at a corner of a box, or if a box has more than one tag, then, in addition to position, the orientation of the box might also be determined and stored in the database. Such a database can also be used to keep track of the individual characteristics of each box, such as the size of the array of slots and the types of sample containers that can be stored in the box. Knowledge of the particular slot array size and configuration and the box's position and orientation can be used to identify the particular reader coils that are relevant to the particular box.

In addition to having ID chips or RFID tags, the boxes, racks, and/or freezers of system 100 may have temperature sensors (integrated within or separate from the corresponding control electronics) that are configured to the corresponding control electronics to enable the control electronics to report temperature measurements to host computer 102, which can be designed to maintain a log of temperature vs. time and/or trip an alarm when temperatures go out of a specified range.

Cold storage system 100 may also be configured with means (such as temperature sensors, conductive tape, and/or light-sensitive sensors) for providing box-interlock/tamper-evident protection.

FIGS. 5-9 show block diagrams of cold storage system 500, according to another embodiment of the present invention. Cold storage system 500 is similar to cold storage system 100 of FIG. 1, except that system 500 has an additional hierarchy level: a shelf level in between the freezer level and the rack level, such that each freezer can have one or more shelves, where each shelf can have one or more racks. Another difference is that, while, in system 100, the warm/cold interface occurs between the freezer level and the rack level, in system 500, the warm/cold interface occurs between the room level and the freezer level, where each freezer has two sets of control electronics: room-level control electronics (504) on the upstream, warm side of the warm/cold interface and freezer-level control electronics (506) on the downstream, cold side of the warm/cold interface.

Figure 5:
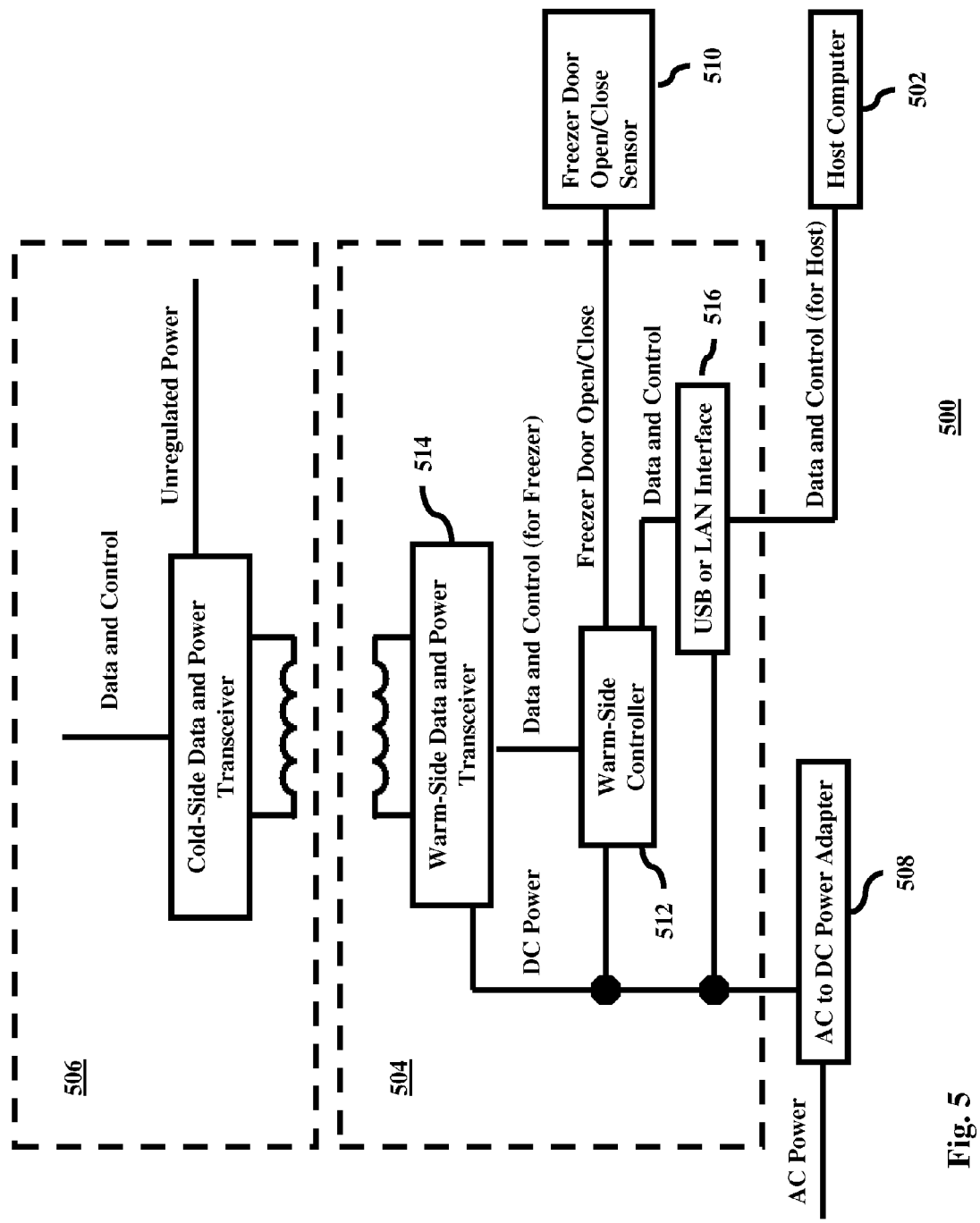
FIGS. 5-9 show block diagrams of the room, freezer, shelf, rack, and box levels, respectively, of a cold storage system according to another embodiment of the present invention.

FIG. 5 represents the room level of cold storage system 500. At the room level, cold storage system 500 has host computer 502 and, for each freezer in system 500, a room-level, warm-side freezer printed circuit board (PCB) 504; a freezer-level, cold-side freezer PCB 506; an AC-to-DC power adapter 508; and a freezer door open/close sensor 510.

Within warm-side freezer PCB 504, controller 512 (e.g., a digital logic, field-programmable logic device, microprocessor, or the equivalent) controls the operations of warm-side freezer PCB 504. Transceiver 514 communicates data to and from and delivers power to the transceiver on cold-side freezer PCB 506 via corresponding inductive coupling coils. If thermal conductivity from direct, ohmic wiring between the warm side and the cold side would be sufficiently low, then transceiver 514 and the corresponding cold-side transceiver can be omitted with warm-side freezer PCB 504 directly wired to cold-side freezer PCB 506. Network interface 516 (e.g., a standard USB or LAN interface) provides a data and control interface to host computer 502, which executes software to manage cold storage system 500.

Power adapter 508, which is energized by externally supplied AC line power, is a commercial off-the-shelf AC-to-DC power adapter that provides regulated DC power to the components of warm-side freezer PCB 504.

Freezer door open/close sensor 510 provides a signal to controller 512 to indicate whether the freezer door is open or closed. This information is relayed to host computer 502 and may be used to stimulate the management software to update the inventory of the system contents.

Warm-side freezer PCB 504 will also typically include conventional PCB components, such as decoupling capacitors and microprocessor oscillators, that are not shown in FIG. 5.

Figure 6:
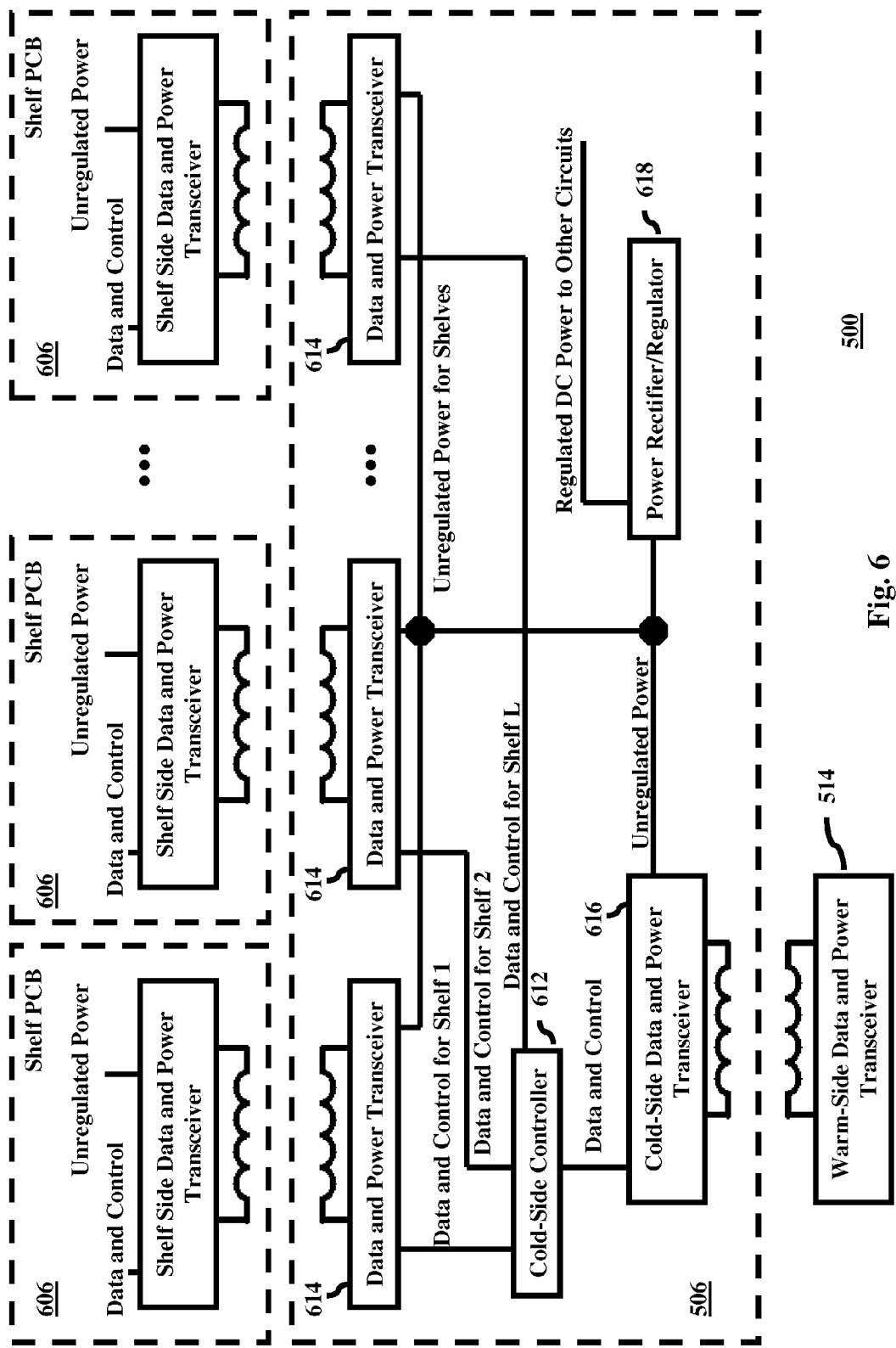

FIG. 6 represents the freezer level of cold storage system 500. At the freezer level, each freezer in cold storage system 500 has cold-side freezer PCB 506 and a shelf PCB 606 for each shelf in the freezer.

Within cold-side freezer PCB 506, controller 612 (e.g., a digital logic, field-programmable logic device, microprocessor, or the equivalent) controls the operations of freezer PCB 506. Transceiver 616 communicates data to and from and receives power from transceiver 514 via corresponding inductive coupling coils. Each transceiver 614 communicates data to and from and delivers power to the transceiver on the corresponding shelf PCB 606 via corresponding inductive coupling coils, which are sufficiently close to one another when the corresponding shelf is fully inserted within the freezer. If the shelves are statically mounted in the freezer, then transceivers 614 and their corresponding transceivers on shelf PCBs 606 can be omitted with cold-side freezer PCB 506 directly wired to each shelf PCB 606. In any case, wiring connects cold-side freezer PCB 506 to locations near each shelf, either to a coupling coil or directly to the shelf.

Unregulated power from transceiver 616 passes into a rectifier and regulator circuit 618. From circuit 618, the other components of cold-side freezer PCB 506, such as controller 612 and each transceiver 614, are powered. This same unregulated power is coupled via transceivers 614 to the shelves in order to power the shelves. On cold-side freezer PCB 506, the control signals to each transceiver 614 can be used to disable power transfer to the respective shelf, such that any subset, from none up to all, of the shelves in the freezer will receive power at any point in time.

Cold-side freezer PCB 506 will also typically include conventional PCB components, such as decoupling capacitors and microprocessor oscillators, that are not shown in FIG. 6.

Figure 7:
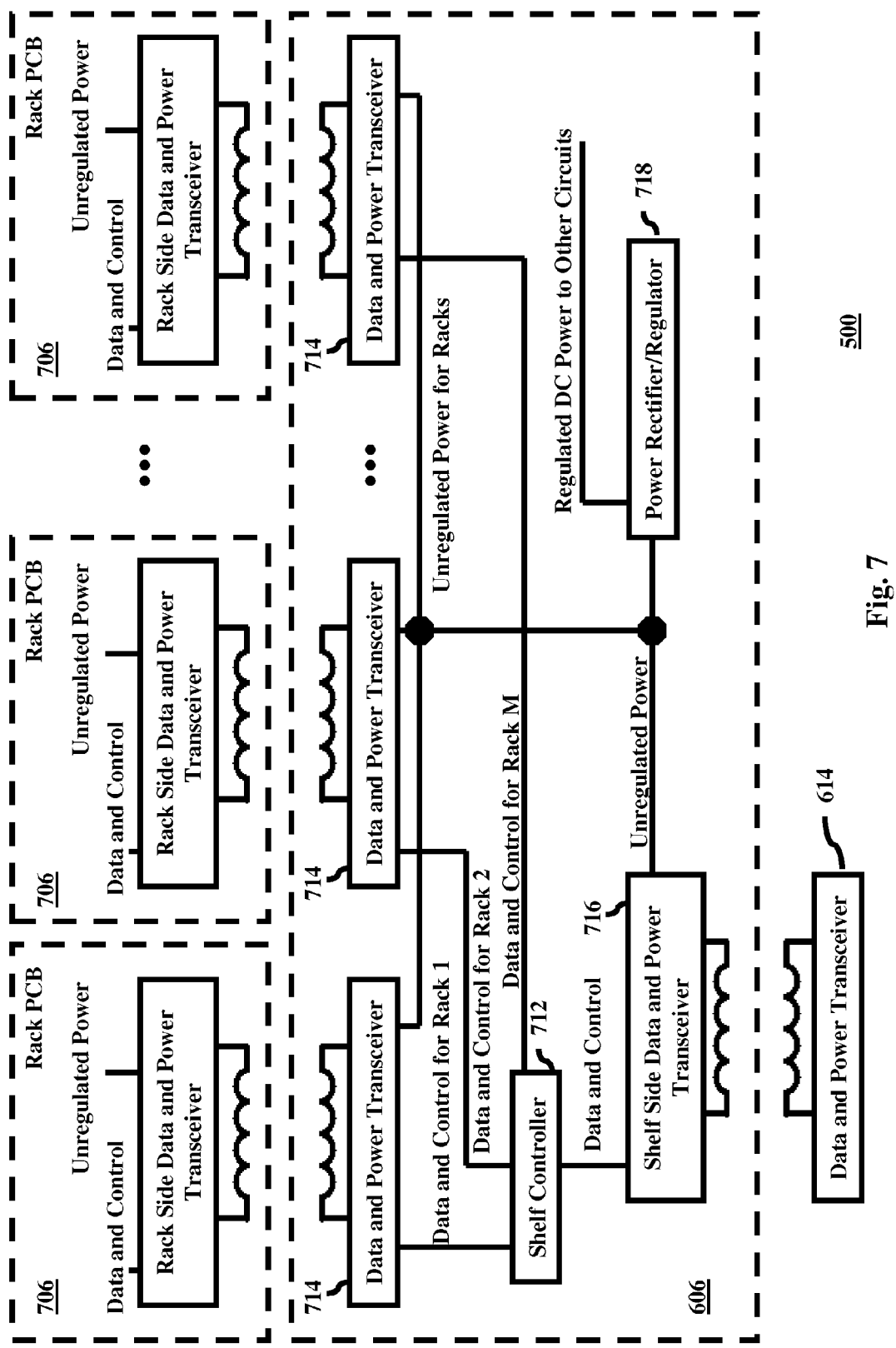

FIG. 7 represents the shelf level of cold storage system 500. At the shelf level, each shelf in cold storage system 500 has shelf PCB 606 and a rack PCB 706 for each rack in the shelf. Shelf PCB 606 may be placed in the back of a standard shelf for holding vial storage racks. The shelf holds one or more racks, which preferably must be fully inserted in order to close the freezer. At standard locations where an inserted rack PCB 706 comes in close proximity to shelf PCB 606, a coupling coil in the rack will come in close proximity to a corresponding coupling coil on the shelf PCB.

Within shelf PCB 606, controller 712 (e.g., a digital logic, field-programmable logic device, microprocessor, or the equivalent) controls the operations of shelf PCB 606. Transceiver 716 communicates data to and from and receives power from transceiver 614 via corresponding inductive coupling coils. Each transceiver 714 communicates data to and from and delivers power to the transceiver on the corresponding rack PCB 706 via corresponding inductive coupling coils, which are sufficiently close to one another when the corresponding rack is fully inserted within the shelf.

Unregulated power from transceiver 716 passes into a rectifier and regulator circuit 718. From circuit 718, the other components of shelf PCB 606, such as controller 712 and each transceiver 714, are powered. This same unregulated power is coupled via transceivers 714 to the racks in order to power the racks. On shelf PCB 606, the control signals to each transceiver 714 can be used to disable power transfer to the respective rack, such that any subset, from none up to all, of the racks in the shelf will receive power at any point in time.

Shelf PCB 606 will also typically include conventional PCB components, such as decoupling capacitors and microprocessor oscillators, that are not shown in FIG. 7.

Figure 8:
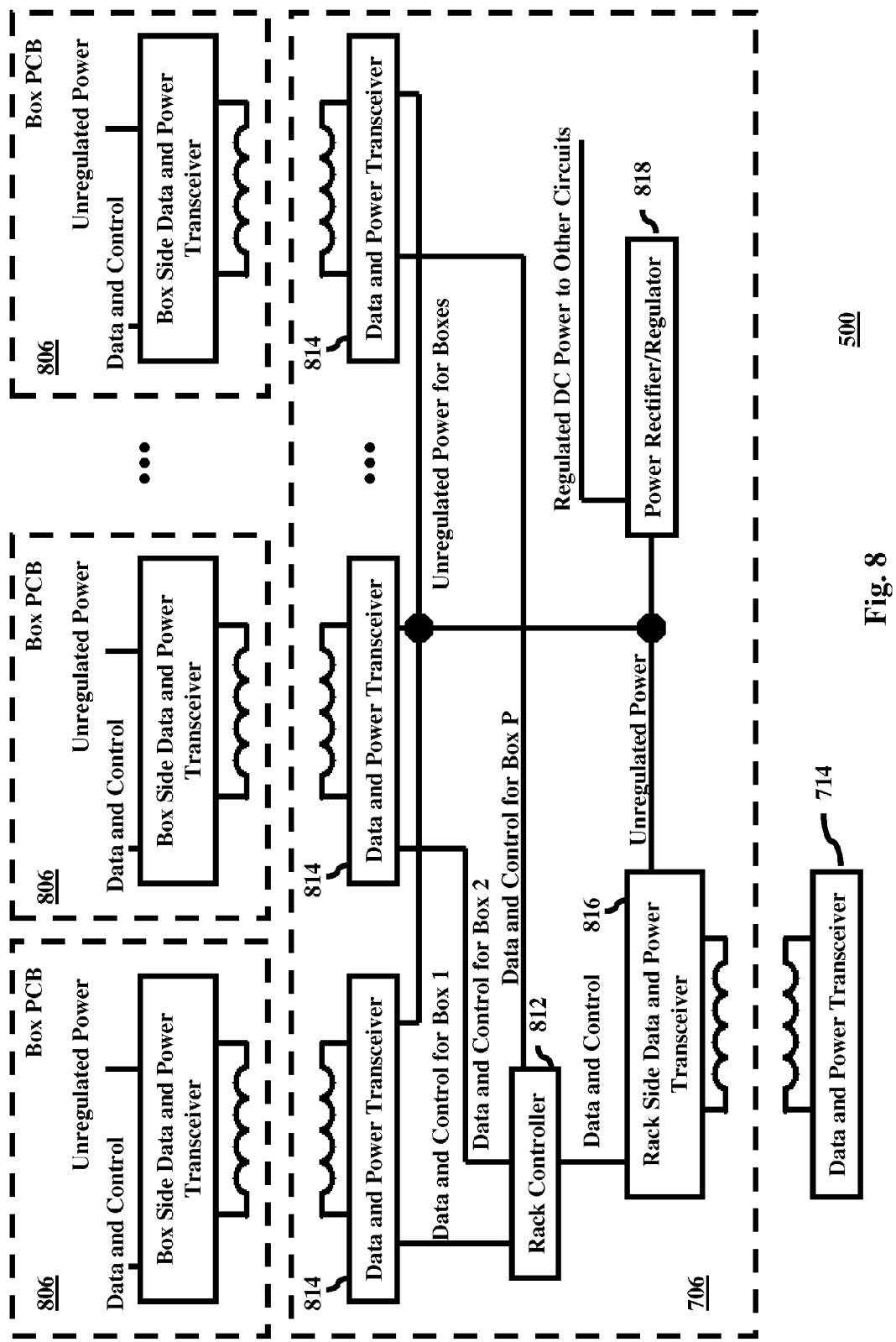

FIG. 8 represents the rack level of cold storage system 500. At the rack level, each rack in cold storage system 500 has rack PCB 706 and a box PCB 806 for each box in the rack. Rack PCB 706 may be placed in the back of a standard rack for holding vial storage boxes. The rack holds one or more boxes, which must be fully inserted to insert the rack in the freezer. At standard locations where an inserted box PCB 806 comes in close proximity to rack PCB 706, a coupling coil in the box will come in close proximity to a corresponding coupling coil on the rack PCB.

Within rack PCB 706, controller 812 (e.g., a digital logic, field-programmable logic device, microprocessor, or the equivalent) controls the operations of rack PCB 706. Transceiver 816 communicates data to and from and receives power from transceiver 714 via corresponding inductive coupling coils. Each transceiver 814 communicates data to and from and delivers power to the transceiver on the corresponding box PCB 806 via corresponding inductive coupling coils, which are sufficiently close to one another when the corresponding box is fully inserted within the rack.

Unregulated power from transceiver 816 passes into a rectifier and regulator circuit 818. From circuit 818, the other components of rack PCB 706, such as controller 812 and each transceiver 814, are powered. This same unregulated power is coupled via transceivers 814 to the boxes in order to power the boxes. On rack PCB 706, the control signals to each transceiver 814 can be used to disable power transfer to the respective box, such that any subset, from none up to all, of the boxes in the rack will receive power at any point in time.

Rack PCB 706 will also typically include conventional PCB components, such as decoupling capacitors and microprocessor oscillators, that are not shown in FIG. 8.

Figure 9:
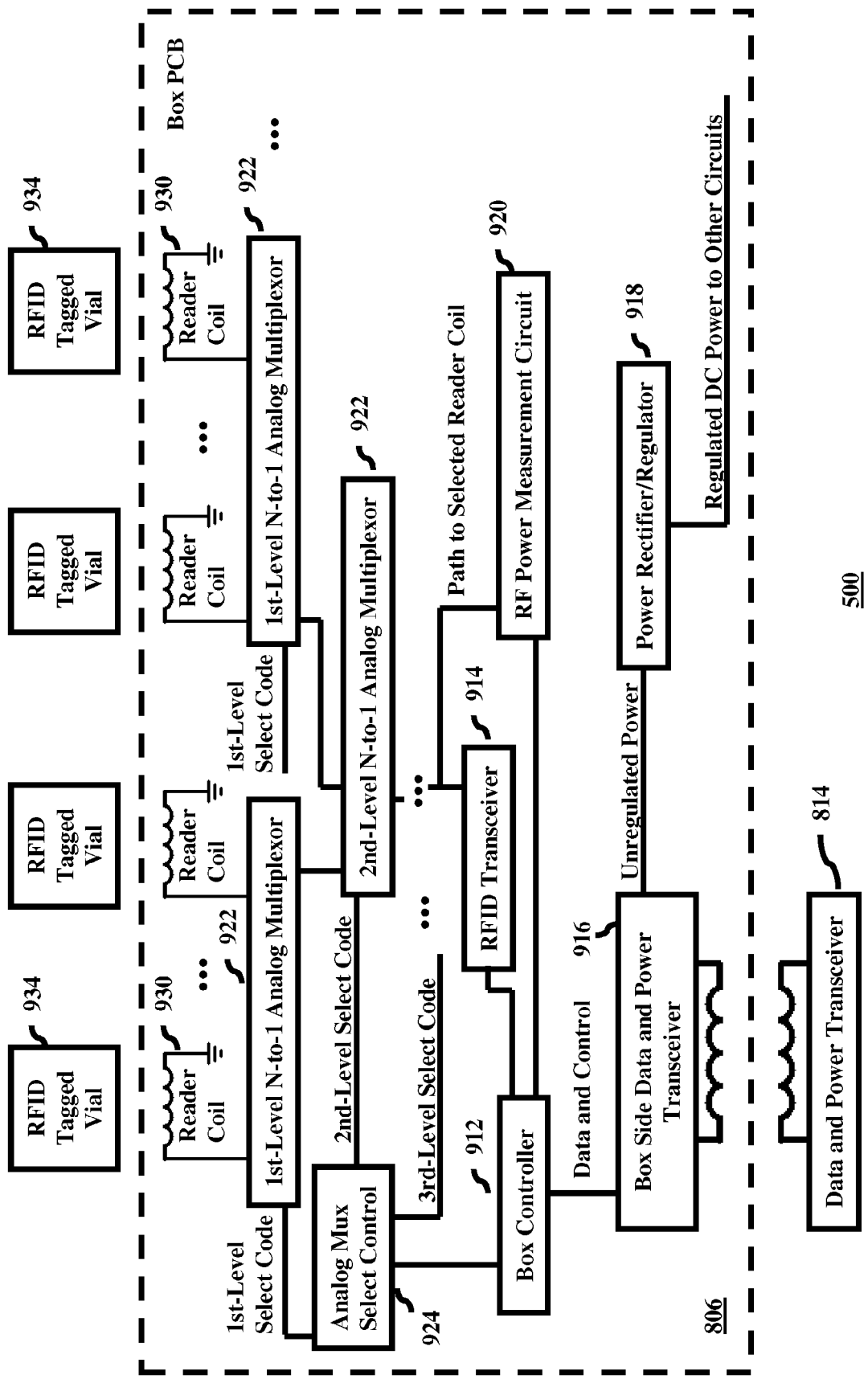

FIG. 9 represents the box level of cold storage system 500. At the box level, each box in cold storage system 500 has box PCB 806 and an RFID tag for each sample container (i.e., vial) 934 in the box. Box PCB 806 may be placed at the bottom of a standard vial storage box or configured at the bottom of a system-specific box. The box stores a regular rectangular array of vials 934, standing on end. At the bottom of each vial is an RFID tag chip with a tag antenna. Incorporated into box PCB 806 is an array of reader antenna coils 930, one per vial tag, where each reader coil 930 is located in close proximity to the corresponding vial tag.

Within box PCB 806, controller 912 (e.g., a digital logic, field-programmable logic device, microprocessor, or the equivalent) controls the operations of box PCB 806. Transceiver 916 communicates data to and from and receives power from transceiver 814 via corresponding inductive coupling coils.

Unregulated power from transceiver 916 passes into a rectifier and regulator circuit 918. From circuit 918, the other components of box PCB 806 are powered.

Box PCB 806 has a hierarchical configuration of bidirectional analog multiplexors (muxes) 922, where the number of levels of muxes, the number of muxes in each level, and the size of each mux depends on the number of reader coils 930 in the box. For example, using 8-to-1 muxes (e.g., NLAS4051 muxes from ON Semiconductor Corporation of Phoenix, Ariz.), a box containing 100 reader coils 930 can be configured with 13 first-level muxes, two second-level muxes, and one third-level mux, where each input of the first 12 first-level muxes is connected to one end of a different reader coil 930, four inputs of the $13^{th}$ first-level mux are connected to the remaining four reader coils 930, the eight inputs of the first second-level mux are connected to the outputs from eight of the first-level muxes, five inputs of the second second-level mux are connected to the outputs from the remaining five first-level muxes, and two inputs of the third-level mux are connected to the outputs from the two second-level muxes.

Mux controller 924 provides appropriate control signals to instruct the various muxes 922 as to which mux input to route to the mux output. In one implementation, muxes within the same level all receive the same control signal.

The output from the highest-level mux is connected to RFID reader transceiver 914 (e.g., S6700 Multi Protocol Transceiver IC (R1-R6C-001A) from Texas Instruments of Dallas, Tex.), which is in turn connected to box controller 912.

Also connected to the output from the highest-level mux is RF power measurement circuit 920, which measures incoming power from the selected tag, to assist in determining which reader coil is nearest to a particular RFID tag.

Only the reader coil 930 on the completely selected path is connected to RFID reader transceiver 914 and power measurement circuit 920. Of 13 reader coils 930 in this example selected by the 13 first-level muxes 922, only one per second-level mux 922 (a total of two), and of these two, only one per third-level mux 922 (a total of one) connects at any one time to RFID reader transceiver 914 and power measurement circuit 920. No other reader coil 930 has a complete circuit path to RFID reader transceiver 914 or power measurement circuit 920.

In addition to being able to transmit an upstream message from a particular reader coil 930 to RFID reader transceiver 914, the configuration of muxes 922 is also able to transmit downstream messages from transceiver 914 to energize each reader coil 930 to query the RFID tag of the corresponding vial 934. Note that the many mux "inputs" and single mux "output" attached to the top and bottom, respectively, of each of the muxes 922 shown in FIG. 9 refer to the upstream direction, in which analog muxes 922 pass data signals detected at reader coils 930 upstream to RFID reader transceiver 914 and RF power measurement circuit 920. As bidirectional devices, analog muxes 922 are also capable of passing data/power signals from transceiver 914 downstream to reader coils 930.

Box PCB 806 will also typically include conventional PCB components, such as decoupling capacitors and microprocessor oscillators, that are not shown in FIG. 9.

Retrofitting Existing Equipment

In one implementation, a cold storage system of the present invention, such as system 100 of FIG. 1, is constructed by modifying existing conventional freezers that do not have freezer control electronics like electronics 110 or coils like coils 114. Such conventional freezers have conventional racks without any rack control electronics like electronics 120 and without any coils like coils 116 and 122, and those conventional racks are typically used to receive conventional boxes without any box control electronics like electronics 128 and without any coils like coils 124 and 130. And those conventional boxes are typically used to house sample containers without any RFID tags like tag 136 and without any coils like coils 132.

To retrofit such a conventional freezer, an instance of freezer control electronics 110 and appropriate coils 114 are added to each freezer to form an instance of freezer 106. In addition, either each conventional rack is replaced by an instance of rack 118 or an instance of rack control electronics 120 and appropriate coils 116 and 122 are added to each conventional rack to form an instance of rack 118.

Although, in theory, existing conventional boxes could be retrofitted to form instances of boxes 126, it is envisioned that the existing conventional boxes will simply be replaced by specifically manufactured instances of boxes 126 in which box control electronics 128 and coils 124 and 130 are integral elements of each box 126.

Significantly, however, since existing biological samples are often expensive and/or irreplaceable, as described below, existing conventional (non-RFID) sample containers that may already store biological samples can be retrofitted to form instances of RFID-enabled sample containers 134, preferably without thawing the frozen biological samples.

Figure 10:
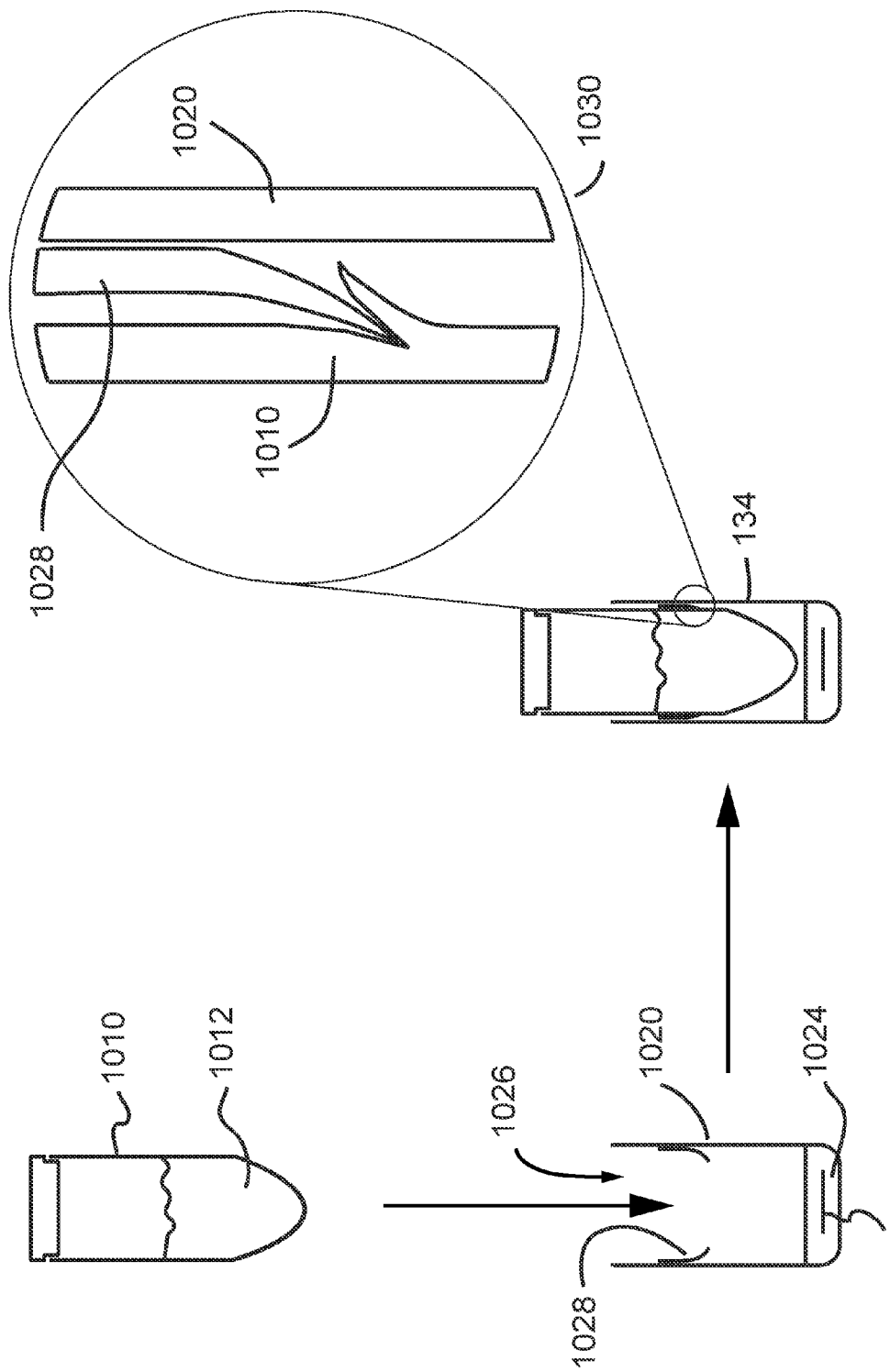
FIG. 10 illustrates one possible scheme for retrofitting an existing, conventional, untagged, plastic sample tube (already storing an biological sample) to form an exemplary sample container of FIG. 1.

FIG. 10 illustrates one possible scheme for retrofitting an existing, conventional, untagged, plastic sample tube 1010 (already storing a biological sample 1012) to form an exemplary sample container 134 of FIG. 1. In particular, sample tube 1010 is inserted into the top opening 1026 of tagged tube 1020, which has an RFID chip 1022 (e.g., RFID electronics 136 with integrated tag antenna coil 132) hermetically sealed within a bottom compartment 1024 of tagged tube 1020, where the inner diameter of tagged tube 1020 is designed to be only slightly larger than the outer diameter of untagged sample tube 1010. In addition, as shown more clearly in the magnified view of inset 1030, the cylindrical inner surface of opening 1026 has a sharp-edged, annular insert 1028 made of spring metal that enables untagged sample tube 1010 to be inserted into tagged tube 1020 with relative ease, but cuts into the plastic material of sample tube 1010 to ensure that sample tube 1010 will be retained within tagged tube 1020 during normal handling of the resulting tube-in-tube assembly.

Figure 11:
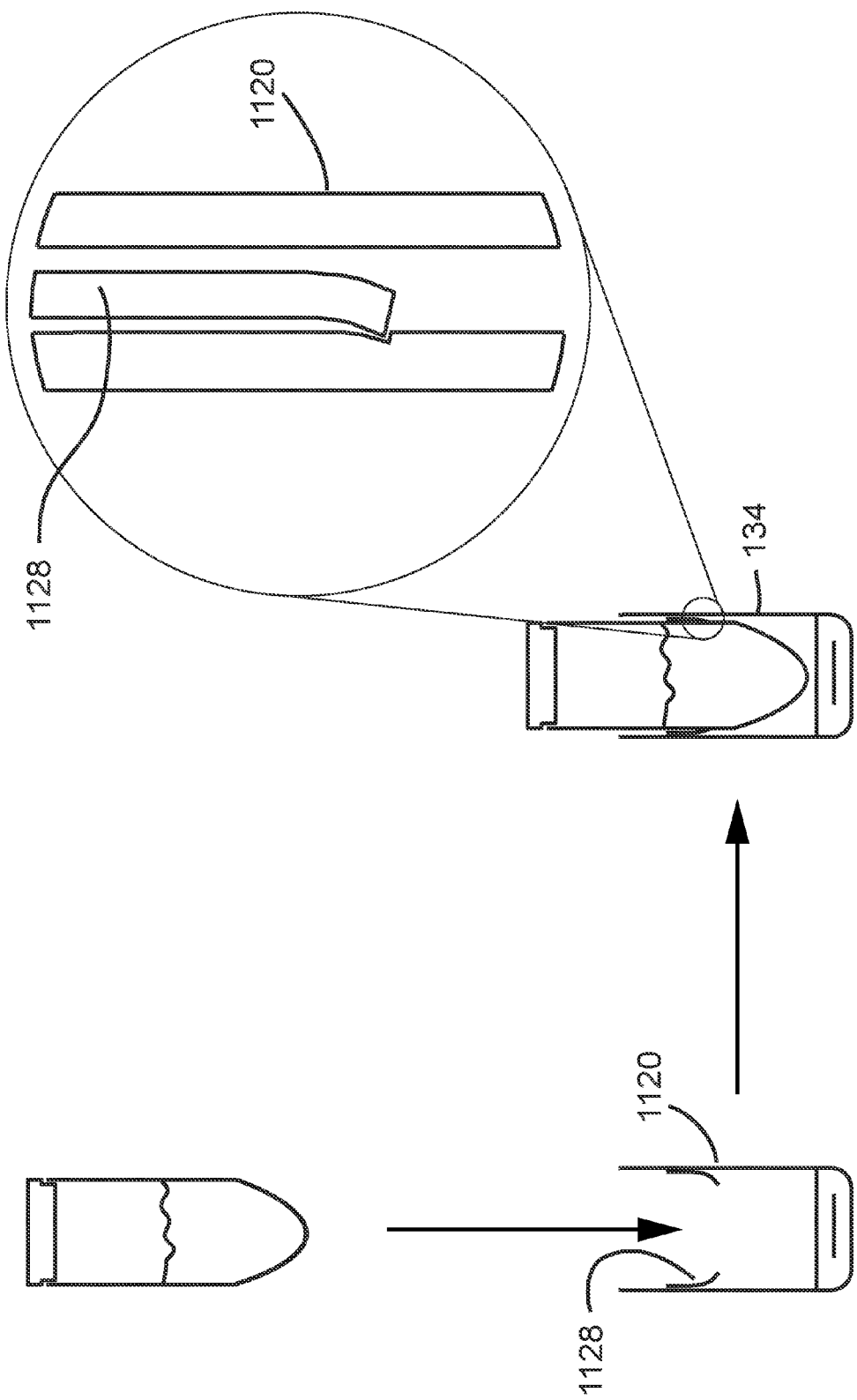
FIG. 11 illustrates another possible scheme for retrofitting existing, untagged sample tubes.
Figure 12:
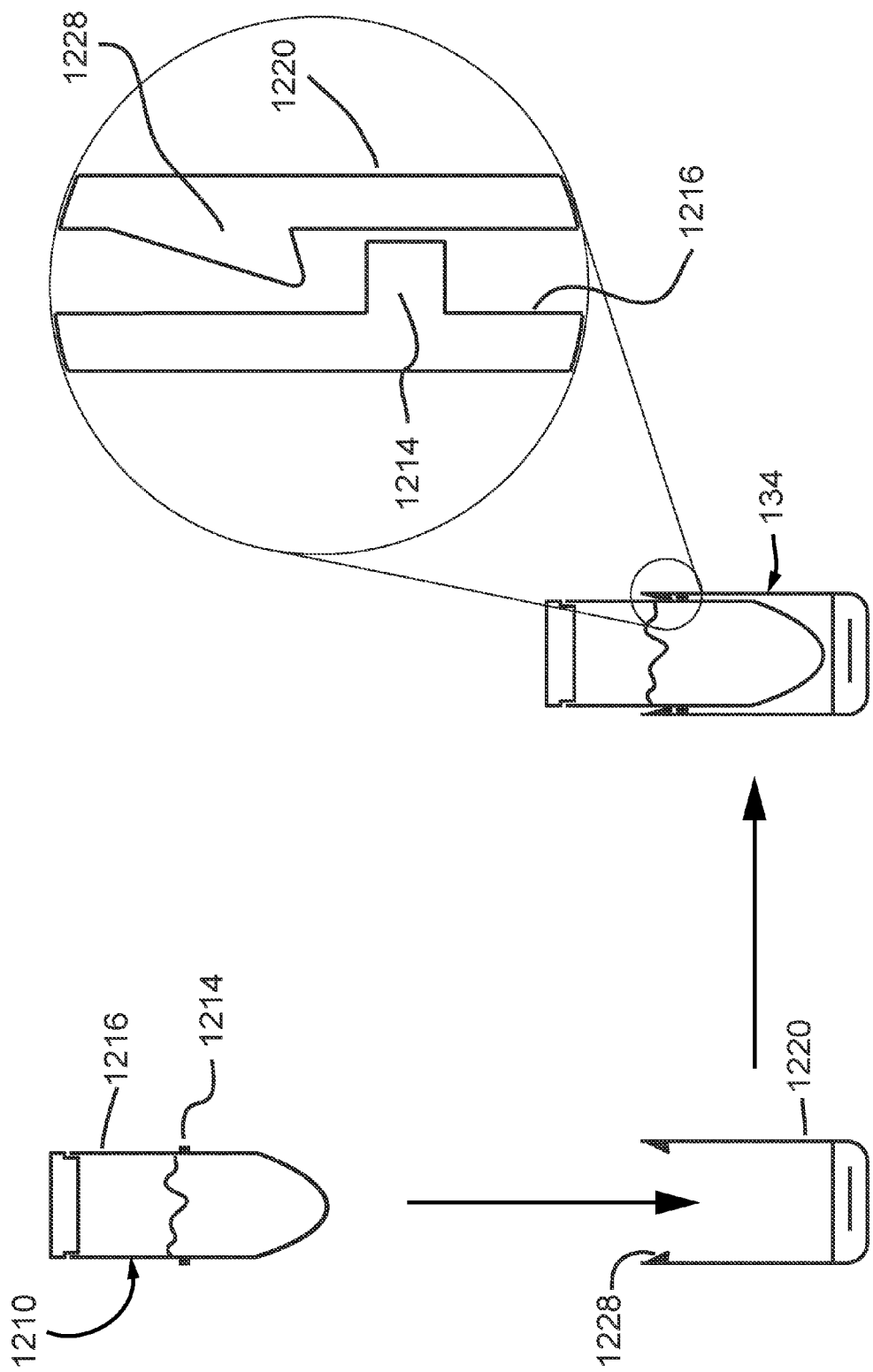
FIG. 12 illustrates yet another possible scheme for retrofitting existing, untagged sample tubes.
Figure 13:
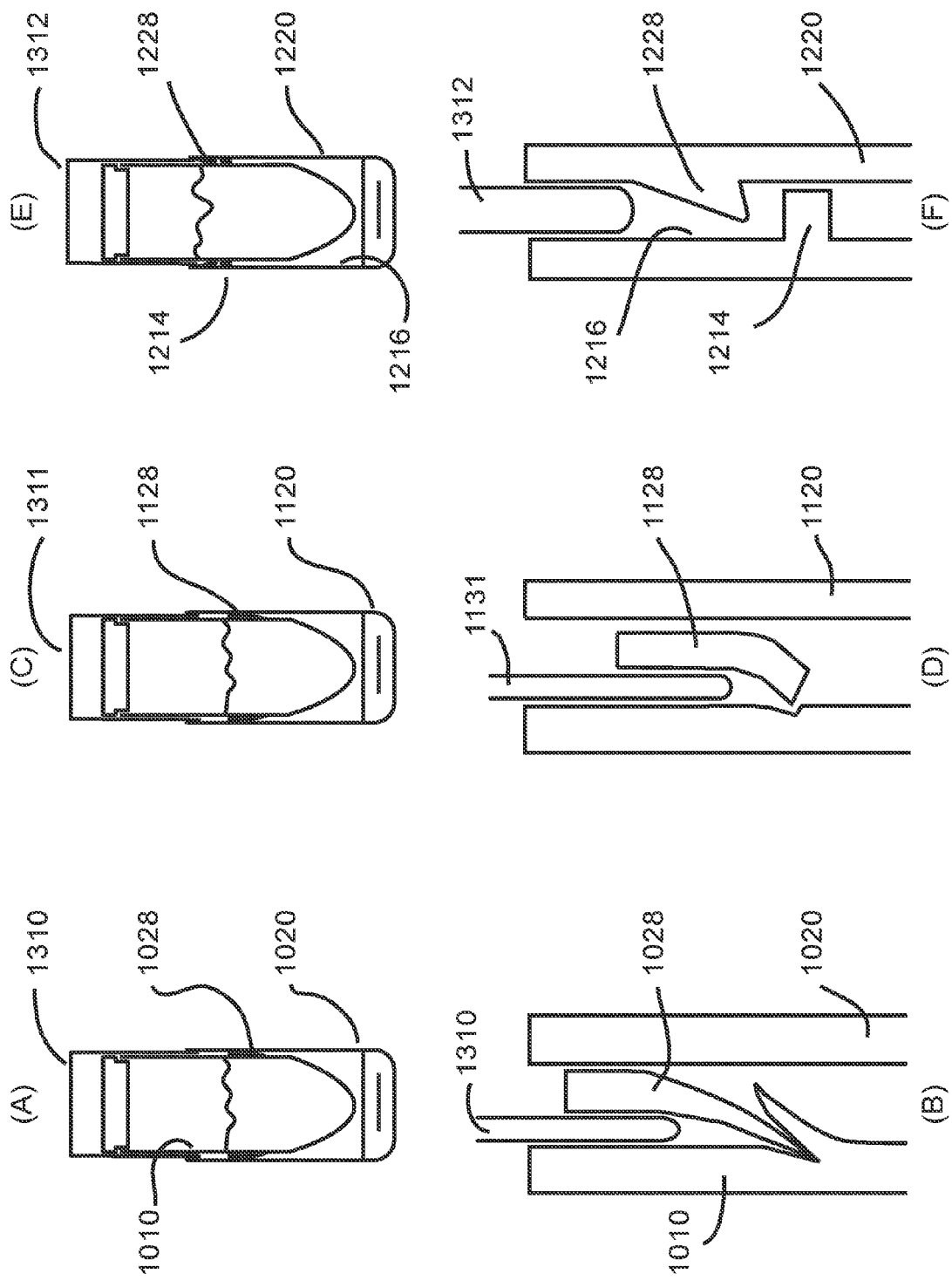
FIG. 13A shows a cross-sectional view of a releasing tool for the retrofitting scheme of FIG. 10.
FIG. 13B shows a cross-sectional view of a portion of the releasing tool of FIG. 13A.
FIG. 13C shows a cross-sectional view of a releasing tool for the retrofitting scheme of FIG. 11.
FIG. 13D shows a cross-sectional view of a portion of the releasing tool of FIG. 13C.
FIG. 13E shows a cross-sectional view of a releasing tool for the retrofitting scheme of FIG. 12.
FIG. 13F shows a cross-sectional view of a portion of the releasing tool of FIG. 13E.

FIG. 11 illustrates another possible scheme for retrofitting existing, untagged sample tubes, where annular metal insert 1128 of tagged tube 1120 is cut flat rather than cut sharp as in insert 1028 of FIG. 10. FIG. 12 illustrates yet another possible scheme for retrofitting existing, untagged sample tubes, where sample tube 1210 has a circular ridge 1214 on its outer cylindrical surface 1216, which ridge is designed to engage an integrated or insertable latch 1228 on the inner cylindrical surface of tagged tube 1220.

In each of these cases, the resulting configuration of untagged sample tube inserted within tagged tube forms an (at least) semi-permanent instance of sample container 134 of FIG. 1.

FIGS. 13A-F shows how, in certain implementations, a releasing tool (e.g., tool 1310 of FIGS. 13A-B, tool 1311 of FIGS. 13C-D, and tool 1312 of FIGS. 13E-F), e.g., in the form of a thin-walled tube, can be inserted between the outer surface of the untagged sample tube and the inner surface of the tagged tube to release the untagged sample tube from the tagged tube, if desired.

Cold storage system 500 of FIGS. 5-9 can be constructed in an analogous retrofitting manner from existing freezers having shelves, racks, and boxes.

Operational Scenarios

In a preferred implementation of cold storage system 100 of FIG. 1, host computer 102 automatically and autonomously maintains a database that maps the ID number of each sample container 134 housed within system 100 to its corresponding current location (e.g., freezer i where $1 \leq i \leq N$, rack j where $1 \leq j \leq M$, box k where $1 \leq k \leq P$, and slot l where $1 \leq l \leq Q$). Host computer 102 is capable of controlling the operations of system 100 to build and update that database as necessary and appropriate. In particular, host computer 102 is capable of instructing each freezer control electronics 110 to instruct each corresponding rack control electronics 120 to instruct each corresponding box control electronics 128 to energize (e.g., sequentially) each of its reader coils 130 to identify the sample container (if any) stored in the corresponding slot.

Depending on the RFID technology, an RFID tag at a particular location can be queried as to its identity by providing it with a full tag ID number (e.g., the tag ID number stored in the database for that location). The tag responds by transmitting an upstream message indicating whether or not the provided tag ID number matches the tag's embedded ID number. If the ID numbers do not match, then conventional RFID technology supports procedures whereby the embedded tag ID number can be retrieved from the tag one bit at a time. The estimated time to verify the presence of one tag is 6.6 ms. Verifying the contents of a typical, fully-loaded freezer storing 20,000 tagged sample containers would take a little over two minutes assuming no tags were moved, removed, or replaced. The time required to learn the ID numbers of all 20,000 tagged sample containers would take a longer time assuming no tags were known before the reading began. However, this is a rare case. In the more typical case, a box of new, removed, or moved tags would cause up to 100 locations to change ID number. About one minute of additional time would be required to learn about these changes in addition to the time required to verify that the bulk of the samples in the freezer have not changed in location.

But this is a worst-case scenario because the tag reading will almost certainly be far more efficient since typically only one RFID tag will reply to a specific query. This is because of the geometry of the system and that appropriately low powers will be used for tag activation. This will likely preclude multiple tags from replying to a query. In addition, box control electronics 128 is designed so that each antenna will deliver sufficient power to the RFID tag so that it is reliably activated but with less power than might activate multiple tags.

In one possible implementation, different operations are implemented sequentially, such that only one RFID tag is accessed at a time. In other implementations, two or more RFID tags may be accessed simultaneously. For example, (1) two or more different reader coils in the same box may be simultaneously energized to access two or more different tags in the same box and/or (2) two or more different boxes on the same rack may be simultaneously operated and/or (3) two or more different racks in the same freezer may be simultaneously operated and/or (4) two or more different freezers in the cold storage system may be simultaneously operated. In this way, many RFID tags may be accessed simultaneously.

FIGS. 14A-D show a flow diagram of exemplary processing implemented within cold storage system 100 of FIG. 1. Optional access-control processing starts at Node Z of FIG. 14A and flows to Node A of FIG. 14A. Standard processing then continues at Node A of FIG. 14B and flows to Node B of FIG. 14B. Processing then continues from Node B of FIG. 14C and flows to Node C of FIG. 14C. Processing then jumps to Node C of FIG. 14D and flows to Node D of FIG. 14D. Processing then returns to Node D of FIG. 14C and flows to Node A of FIG. 14C, from which point processing returns to Node A of FIG. 14B to repeat the processing of FIGS. 14B-D.

Figure 14A:
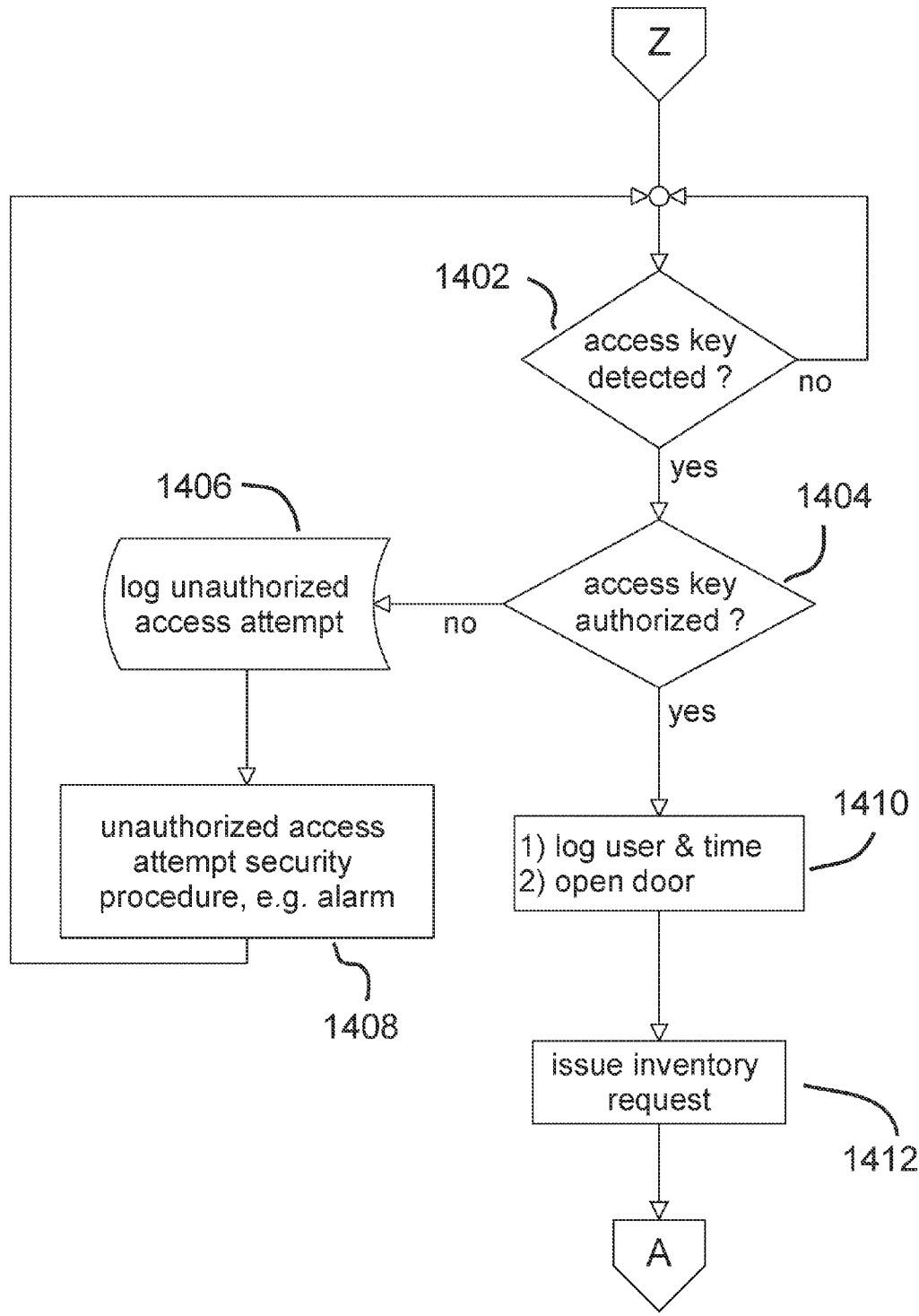
FIGS. 14A-D show a flow diagram of exemplary processing implemented within the cold storage system of FIG. 1.
Figure 14B:
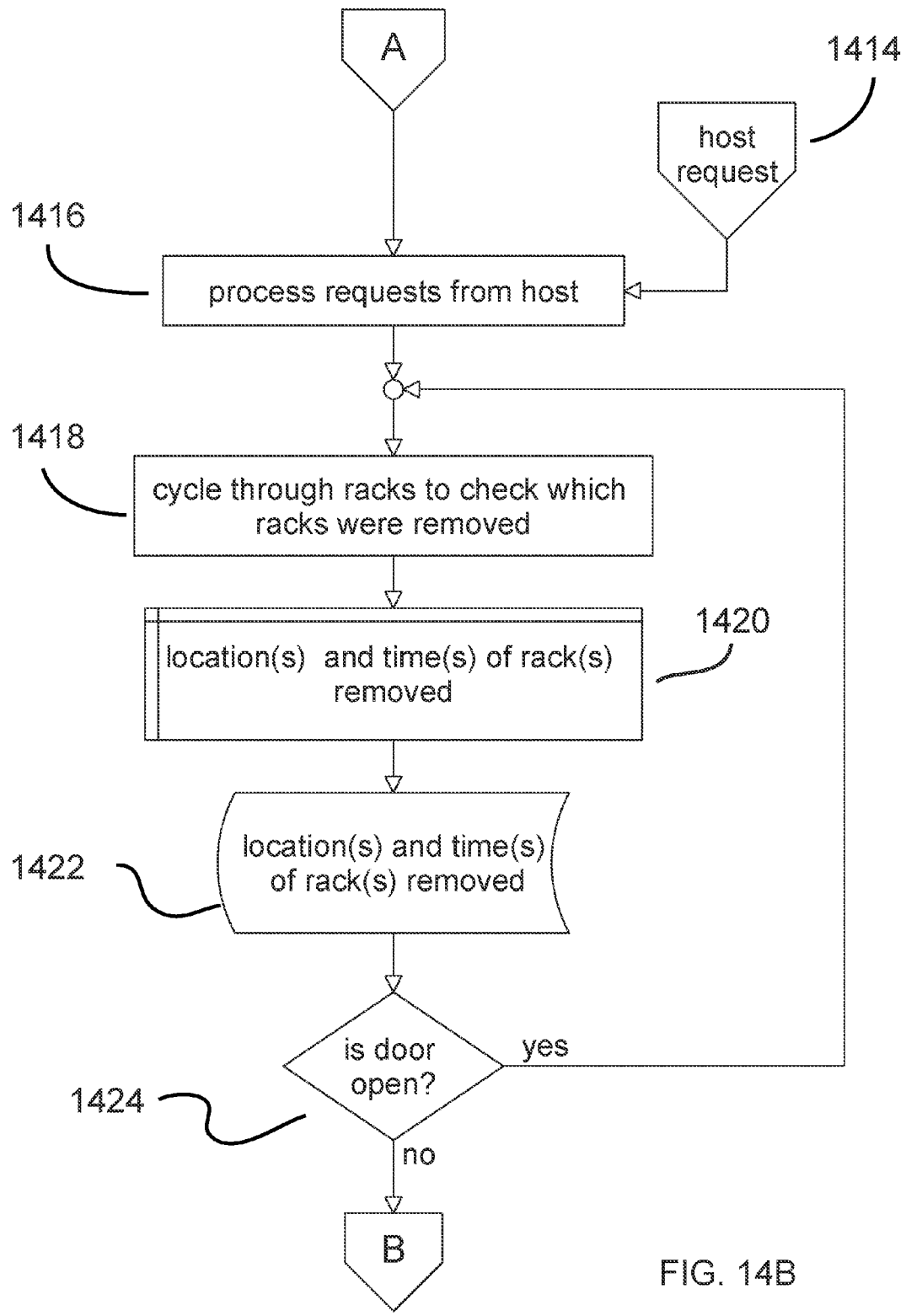
Figure 14C:
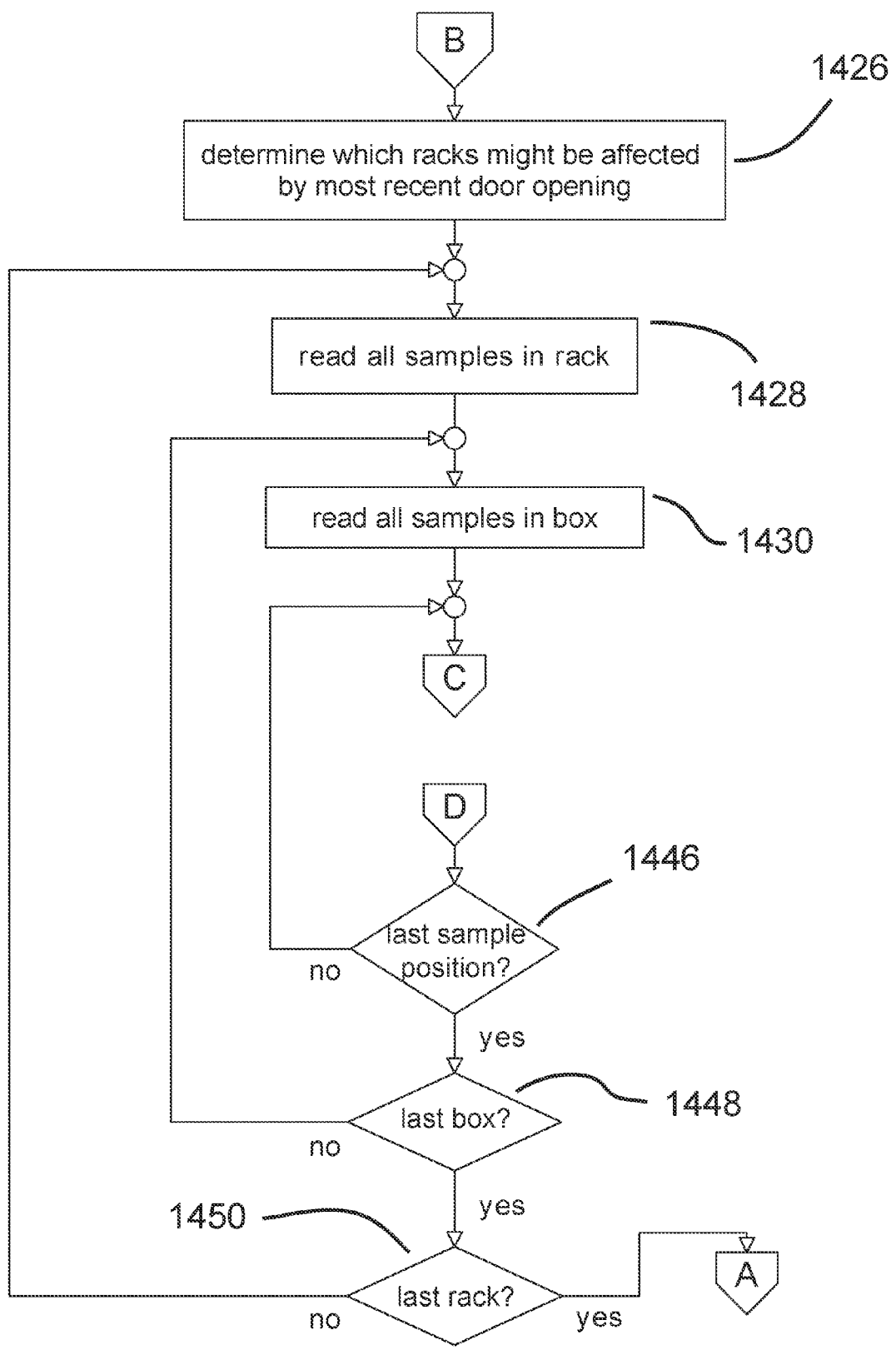
Figure 14D:
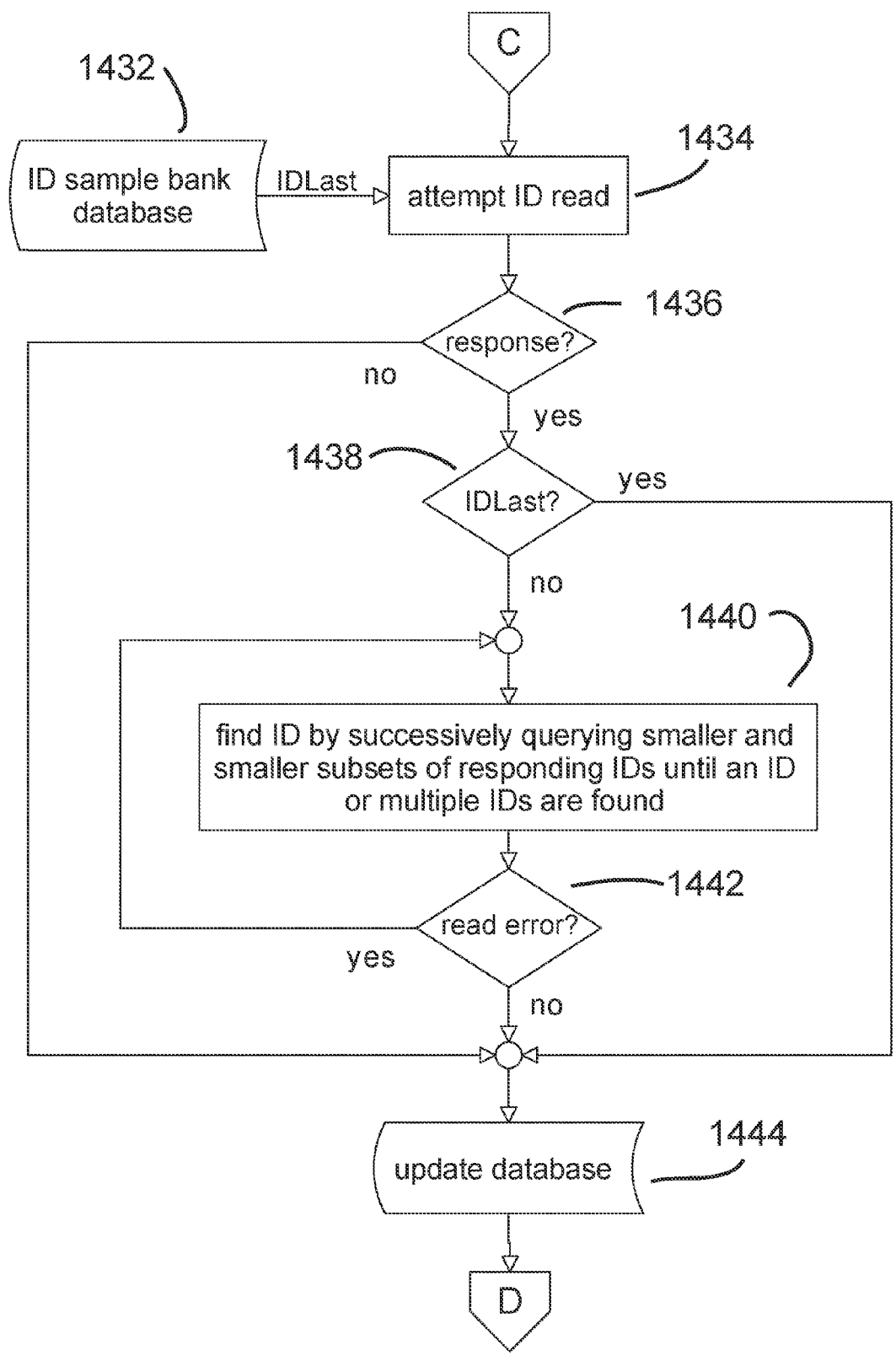

The standard inventory processing of FIGS. 14B-D is stimulated by various other subprocessing, including the access-control processing of FIG. 14A. These processes include event-triggered processes, such as the depicted access-control routines. Other processes may be initiated by events not depicted, such as but not limited to (a) an uncontrolled door opening, (b) routine maintenance, and (c) chain-of-custody commands. All of these other subprocesses likewise generate an inventory request to be handled by standard inventory processing.

In particular, host computer 102 of FIG. 1 receives (step 1414 of FIG. 14B) and processes (step 1416) a request for routine processing for a particular freezer 106 in cold storage system 100. For example if the door of the freezer was opened, host computer 102 then begins a procedure to cycle through those racks in the freezer that were removed to determine if there were any changes to the sample containers 134 stored in those racks (step 1418). In particular, host computer 102 determines the location(s) and time(s) of rack(s) removed (step 1420) and stores that information in its database (step 1422). If the freezer door is still open (step 1424), then processing returns to step 1418 to continue determining which if any racks are removed.

If the freezer door is not open (step 1424), then host computer 102 determines which racks might have been affected by the most-recent door opening (step 1426 of FIG. 14C). In general, samples and boxes can be removed from a rack that is adjacent to a rack that was physically removed. Since racks are typically five-sided with no right wall, it may be safe to check the rack to the left of the one that was removed. To cover atypical cases, other racks, such as the rack to the right of the one that was removed, might also be tested.

Host computer 102 begins a procedure in which all of the samples in each affected rack are identified (step 1428), which involves identifying all of the samples in each box of each affected rack (step 1430). Steps 1446, 1448, and 1450 perform appropriate comparisons to sequentially identify the sample at each position of each box of each affected rack.

To identify the sample at a particular position in a particular box on a particular rack, host computer 102 retrieves the sample's tag ID stored in its database for that position, IDLast (step 1432 of FIG. 14D). Host computer 102 then transmits commands to freezer control electronics 110 of the corresponding freezer 106 in order to query the tag of the sample container at the particular position as to whether the sample ID retrieved from the database matches the ID of the tag (step 1434). In turn, freezer control electronics 110 transmits appropriate commands to rack control electronics 120 of the corresponding rack, which in turn transmits appropriate commands to box control electronics 128 of the corresponding box, which in turn energizes the appropriate reader coil 130 to query the corresponding tag 136. If there is no tag response detected (step 1436), then the assumption is that there is no sample container at this location and processing proceeds to step 1444, where host processor 102 is instructed to update its database accordingly.

If a tag response is detected (step 1436), then the box control electronics determines whether the tag response indicates that the sample ID retrieved from the database and applied to the reader coil matches the tag's ID (step 1438). If so, then processing proceeds to step 1444.

If the tag response indicated that there is no match (step 1438), then box control electronics initiates a procedure to determine the tag's ID (step 1440). If a read error occurred during that procedure (step 1442), then processing returns to step 1440 to repeat the procedure. If there is no read error, then processing continues to step 1444.

The access-control subprocess of FIG. 14A runs in parallel to the standard inventory process. Host computer 102 starts the access-control subprocess at Node Z of FIG. 14A. If host computer 102 does not detect an access key, electronic or otherwise (step 1402), then processing returns to Node Z to await the next access attempt. If host computer 102 does detect an access key (step 1402), then host computer 102 determines whether the access key is authorized (step 1404). If not, then host computer 102 logs the unauthorized access attempt (step 1406), executes an unauthorized access attempt security procedure (step 1408), and returns to Node Z.

If the access key is authorized (step 1404), then host computer 102 enables the door to be opened and logs the user and access time in its database (step 1410). Host computer 102 then issues an inventory request to the standard inventory process (step 1412). The request is processed beginning at Node A of FIG. 14B as described previously.

Those skilled in the art will understand that the processing of FIGS. 14A-D corresponds to one possible operational scenario for a cold storage system like system 100 of FIG. 1. Many other operational scenarios are also possible, including those designed to initially acquire or re-acquire all of the sample IDs in one or more boxes, one or more racks, one or more freezers, or even the entire system.

The above concepts are illustrated in FIGS. 15A-D. Here, one possible embodiment of a tag addressing scheme is shown in FIG. 15A. In this embodiment, each database entry includes a 2-character data type tag 1502, for example "SA" in FIG. 15A, indicating that this is a sample location. For data type SA, data type tag 1502 is followed by a sample tag 1504 comprising a 21-character physical location field 1506, which identifies the location of the sample, and a 24-character sample ID field 1508, which contains the sample's RFID number. Physical location field 1506 includes a unique 12-character freezer serial number 1510, a 2-character shelf identifier 1512, a 2-character rack identifier 1514, a 2-character box identifier 1516, and a 3-character position identifier 1518 corresponding to the coordinates within the sample box. In this embodiment, position identifier 1518 is in the form of a 1-character row letter and a 2-character column number. Note that, in this embodiment, each character in sample ID field 1508 and freezer serial number 1510 is a hexidecimal value from 0 to F. Colon separators are included for clarity, but are not necessary. In general, the number of characters per field and/or the types of characters used may be different for different embodiments. Also, an embodiment having a different number of hierarchy levels will have a corresponding different number of fields.

The inventory information and the door events could be separated into different files as needed. Similarly, separate files may, or may not, be maintained for different freezers.

FIG. 15B shows a portion corresponding to lines 00419-00441 of an exemplary sample database for a freezer whose serial number is 9A2158749F64. Line 00419 shows a freezer door opening event, indicated by the data type "DO" and the freezer's 12-character serial number along with a time stamp (i.e., consisting of 4-character year, 2-character month, 2-character day, 2-character hour, 2-character minute, and 2-character second) indicating the time of the event and the 24-character serial number of the RFID tag of the user who opened the freezer door.

Personnel are authorized by verifying their identity using any of a variety of technologies such as waving an ID card near an antenna on the freezer or somewhere nearby, by swiping an ID card through a magnetic card reader, or even using biometric verification (fingerprints, iris pattern, etc.) as might be appropriate where a high level of security is required. In all of these cases, the door latch would be unlocked if the ID matches an entry in a database of authorized personnel. Some systems might not include these features.

Line 00420 shows a door closing event, indicated by the data type "DC," the freezer serial number, and a time stamp. Immediately following the door closing an inventory was triggered, as indicated by the data type "IT," along with a time stamp as indicated in line 00421. Beginning in line 00422, the database catalogs a sequential inventory of the freezer contents beginning with the first position in the first box on the first rack on the first shelf in the freezer.

In FIG. 15C, an inventory request from the host system is received by freezer C574243A3D91. This is indicated by an "IR" in the data type along with a time stamp in line 00001. The freezer then scans the contents of the freezer and generates the requested inventory. While the inventory could be performed sequentially through every sample position in the freezer, as shown in FIG. 15B, this might not be the most efficient way of surveying the freezer contents. This is reflected by the seemingly random access to possible sample positions in FIG. 15C. The exact strategy of how best to perform an inventory will depend on the details of a specific implementation of the hardware and software.

FIG. 15D shows a portion of the database for freezer E529E9886A7C. In line 06182, the freezer door was opened, as indicated by the data type "DO" along with the freezer serial number, a time stamp, and the 24-character serial number of the RFID tag of the user who opened the freezer door. Line 06183 shows a door closing "DC" event with the freezer serial number and an associated time stamp. In this case, no inventory was triggered.

For compatibility with other systems and/or for additional security, a human-readable label and/or machine-readable (e.g., bar-code) label can be added to each sample tube. This will protect the integrity of the sample archive in case of tag failure or a system-wide failure of some other kind (e.g., massive, system-wide prolonged power failures, internet failure, such as those that might be experienced during earthquakes, etc.). In this case, the sample archive would revert to the present state of the art.

If the system has some form of network capability, e.g., internet, this capability can be used to relay information about the status of the freezers to the host computer. This might include but is not limited to, freezer temperature, freezer thermal load, as might be inferred from the cooling system duty cycle, unlocked doors, etc.

The system can calculate the empty space in any given freezer and help the user know where to store a set of samples of a given size to optimize sample aggregation, etc.

The system described may rely heavily on the associated database in the following sense: Information about a sample, its location, contents, source, or provenance, even the nature of the sample itself, is not stored in the transponder associated with that sample. Rather, that transponder contains a relatively simple identifying number or code. All of the information about that sample is kept in the associated sample database.

In certain embodiments, the system described here does not incorporate wireless RFID-type transponders except at the sample level. Communication from the box/rack/shelf is done using either wired or magnetic/inductive data transfer. An important reason for this implementation is to avoid direct Ohmic connections. But it has the additional benefit of avoiding data collision issues of a wireless system in a freezer that can contain more than 20,000 samples. Moreover, this issue is avoided by giving an antenna at every possible sample location. Reading from these antennae can be done sequentially or, if no possibility of incorrect reads exists (as was shown is indeed the case in the described system), they can be read simultaneously at several locations. This will decrease the time needed to scan the whole freezer.

Because of its organization, the system does not need to deal with situations of some samples/boxes/racks/shelves not being accessible for reading. In addition, the hierarchy can be set from the onset and does not need to be established by the system in an ongoing basis.

Alternative Embodiments

Although the detailed description has focused mainly on cold storage system 100 of FIG. 1 and cold storage system 500 of FIGS. 5-9, certain features and elements of systems 100 and 500 can be used to implement other storage systems, including:

Systems that have hierarchies other than the freezer/rack/box hierarchy of FIG. 1 and the freezer/shelf/rack/box hierarchy of FIG. 5, including those with fewer or more levels;

Systems that store non-biological samples at low temperatures;

Systems that store biological or non-biological samples at temperatures other than low temperatures, e.g., cell cultures and plant seedlings. As used in this specification, the generic term "cabinets" refers to both the freezers of cold storage applications as well as to the corresponding elements in non-cold (e.g., room temperature or higher) storage applications. In general, freezers can be any type of cabinet that controls the temperature of its contents to be lower than the ambient (e.g., room) temperature, including chest freezers, upright freezers, refrigerators, liquid-nitrogen freezers or cryostats, carbon dioxide freezers, and nitrogen-gas freezers. For high-temperature applications, cabinets may control the temperatures of their contents to be higher than ambient temperature;

Systems that communicate with sample containers using remote communication technology other than RFID technology, including but not necessarily limited to those based on radar-like coupling via far-field reflection; near-field, transformer-like magnetic induction; closely coupled magnetic induction (e.g., between poles of a solid-core transformer); electric dipole antenna transmission; or capacitive coupling.

Systems that rely on separate paths for data transmission and power provisioning, such as two different pairs of coils: one pair for inductively coupled data transmission and a second pair for inductively coupled power provisioning;

Systems that employ direct ohmic (e.g., wired) electrical or other types of non-ohmic (e.g., wireless RF or optical) connections between certain adjacent hierarchy levels. For example, in system 100, instances of rack control electronics 120 could be hard-wired to their corresponding freezer control electronics 110, while maintaining the non-ohmic, inductive magnetic coupling between the rack level and the box level and between the box level and the sample container level;

Systems that rely on battery power, e.g., using active RFID tags, rather than inductive power transfer to passive, reader-powered RFID tags. Batteries may also be used to power one or more other hierarchy levels;

Systems that have ratios of reader coils to possible tag coils other than 1:1. Rather than providing a single reader coil for each possible tag location, one scheme relies on triangulation processing of signals (e.g., Ultra Wide Band) to locate a tag based on the times of flight for an upstream signal received at three or more different reader coils, where a number of reader coils supports a greater number of possible tag locations.

Systems that have an LED on each rack and/or box to verify to the user that the rack or box has been properly placed into the freezer;

Systems that have (1) different numbers and/or sizes of racks in different freezers and/or (2) different numbers and/or sizes of boxes on different racks and/or (3) different numbers and/or sizes of sample containers in different boxes;

Systems that employ sample containers having shapes other than cylindrical and/or materials other than plastic. A typical sample container is a plastic tube with a screw-on or snap-on lid, but sample containers may also include any other means for storing biological or non-biological samples, including, but not limited to, paraffin blocks.

Systems that have tagged collections of tagged samples;

Systems storing collections of high-value items stored in normally inaccessible or dangerous environments, including but not limited to radioactive environments, non-breathable atmosphere environments, liquid environments, and high-temperature environments;

Systems in which some or all of the electronics are heated but insulated from the cold environment to ensure proper operation of the electronic circuits; and Systems in which a box of samples contains a tag (the "box tag") that contains information about its layout, including, but not restricted to, the box dimensions and how the sample vials are divided within the box. Typically, the box tag can be placed in a corner of the box. In different embodiments, the tag can be perpendicular or parallel to the bottom of the box and possibly be mounted on a side wall of the box. The information on the box tag would provide information to the sample tube reader where to expect the enclosed vials. For example, a box divided in a (4×4) pattern would have different vial locations than a box divided in a (3×3) pattern. The box tag would tell the reader where to look for the tagged sample tubes. In addition, the box tag would announce to the whole sample storage system where the box is located within a particular freezer. In one embodiment of this method, the box tag would be read first, possibly by looking at each corner until a box tag is found. Anti-collision techniques can be used to read the box tag and any possible vial tag located directly above it. From the position of the box tag, the system software can deduce (a) the location of the box in the freezer, (b) the orientation of the box, and (c) all vial locations.

Unless explicitly stated otherwise, each numerical value and range should be interpreted as being approximate as if the word "about" or "approximately" preceded the value of the value or range.

It will be further understood that various changes in the details, materials, and arrangements of the parts which have been described and illustrated in order to explain the nature of this invention may be made by those skilled in the art without departing from the scope of the invention as expressed in the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

We claim:

1. A system for storing samples, the system comprising at least one first cabinet, at least one first box, and one or more sample containers, wherein:

the first cabinet comprises first cabinet control electronics and is configured to receive the first box;

the first box comprises first box control electronics and is configured to receive the one or more sample containers, each sample container comprising container electronics and configured to store a sample;

the first box control electronics is configured to communicate with the container electronics of each sample container received by the first box;

the container electronics of each sample container is configured to communicate sample-identification information for the sample stored in the sample container to the first box control electronics;

the first box control electronics is configured to communicate the sample-identification information towards the first cabinet control electronics;

the first cabinet control electronics is configured to communicate the sample-identification information to a host computer for the system;

each container electronics is an RFID tag having an associated tag coil;

the first box has at least one reader coil associated with each sample container received by the first box; and the first box has a plurality of slots, each slot having an associated reader coil, such that, if a sample container is inserted within a slot, the associated reader coil is configured to energize the tag coil of the corresponding slot to activate the associated RFID tag.

2. The system of claim 1, wherein the system further comprises one or more other instances of the first cabinet.

3. The system of claim 1, wherein the system further comprises one or more other instances of the first box configured to be received by the first cabinet.

4. The system of claim 1, wherein:

the system further comprises at least one first rack;

the first rack comprises first rack control electronics and is configured to receive the first box;

the first rack control electronics is configured to communicate with the first box control electronics;

the first box control electronics is configured to communicate the sample-identification information to the first rack control electronics; and the first rack control electronics is configured to communicate the sample-identification information towards the first cabinet control electronics.

5. The system of claim 4, wherein the system further comprises:
one or more other instances of the first rack configured to be received by the first cabinet; and
one or more other instances of the first box configured to be received by the plurality of instances of the first rack.

6. The system of claim 4, wherein:
the system further comprises at least one first shelf;
the first shelf comprises first shelf control electronics and is configured to receive the first rack;
the first shelf control electronics is configured to communicate with the first rack control electronics;
the first rack control electronics is configured to communicate the sample-identification information to the first shelf control electronics; and
the first shelf control electronics is configured to communicate the sample-identification information towards the first cabinet control electronics.

7. The system of claim 6, wherein the system further comprises:
one or more other instances of the first shelf configured to be received by the first cabinet; and
one or more other instances of the first rack configured to be received by the plurality of instances of the first shelf; and
one or more other instances of the first box configured to be received by the plurality of instances of the first rack.

8. The system of claim 1, wherein:
the system is a cold storage system; and
the first cabinet is a first freezer having first freezer control electronics, wherein the first freezer control electronics are the first cabinet control electronics.

9. The system of claim 8, wherein:
the first freezer comprises a first-temperature side having a first temperature; and
each container electronics and the first box control electronics are housed within the first-temperature side of the first freezer.

10. The system of claim 9, wherein:
the communications between the container electronics of each sample container and the first box control electronics are implemented using non-ohmic coupling; and
the communications between the box control electronics and the first freezer control electronics are implemented using non-ohmic coupling.

11. The system of claim 10, wherein:
the non-ohmic coupling between the first freezer control electronics and the first box control electronics transfers operating power from the first freezer control electronics to the first box control electronics; and
the non-ohmic coupling between the first box control electronics and the container electronics of each sample container transfers operating power from the box control electronics to the container electronics.

12. The system of claim 9, wherein:
the first freezer further comprises a second-temperature side having a second temperature greater than the first temperature; and
the first freezer control electronics is housed within the second-temperature side of the first freezer.

13. The system of claim 1, wherein the first box control electronics is implemented on a printed circuit board within which is integrated each corresponding reader coil.

14. The system of claim 1, wherein:
the first cabinet control electronics are configured to communicate with the first box control electronics via corresponding non-ohmic coupling; and
the first box control electronics are configured to communicate with the container electronics of each corresponding sample container via corresponding non-ohmic coupling.

15. The system of claim 14, wherein each instance of non-ohmic coupling is inductive magnetic coupling.

16. The system of claim 14, wherein:
the first cabinet control electronics are configured to transfer operating power to the first box control electronics box via the corresponding non-ohmic coupling; and
the first box control electronics are configured to transfer operating power to the container electronics of each corresponding sample container via the corresponding non-ohmic coupling.

17. The system of claim 1, wherein:
the system further comprises at least one first sample container; and
the first sample container comprises (i) an untagged tube containing the sample and (ii) a tagged tube containing the container electronics, wherein the untagged tube is inserted within the tagged tube.

18. The system of claim 17, wherein the tagged tube comprises a mechanism that engages structure of the untagged tube to retain the untagged tube within the tagged tube.

19. The system of claim 18, wherein the mechanism comprises an insert that cuts into structural material of the untagged tube to retain the untagged tube within the tagged tube.

20. The system of claim 18, wherein the untagged tube comprises a ridge that engages with the mechanism to retain the untagged tube within the tagged tube.

21. The system of claim 18, wherein the untagged tube is configured to be released from the tagged tube by inserting a releasing tool between the structure of the untagged tube and the mechanism of the tagged tube.

22. The system of claim 1, wherein the system further comprises the host computer.

23. The system of claim 22, wherein the host computer is configured to control operations of the system to autonomously identify each sample stored within the system.

24. The system of claim 23, wherein the host computer is configured to autonomously identify each sample stored within the system by causing each container electronics to be individually queried to provide its corresponding sample-identification information.

25. The system of claim 1, wherein the sample-identification information uniquely identifies each sample.

26. The system of claim 4, wherein:
the system is a cold storage system;
the first cabinet is a first freezer having first freezer control electronics, wherein the first freezer control electronics are the first cabinet control electronics;
the first freezer comprises a first-temperature side having a first-temperature;
each container electronics and the first box control electronics are housed within the first-temperature side of the first freezer;
the communications between the container electronics of each sample container and the first box control electronics are implemented using non-ohmic coupling;
the communications between the box control electronics and the first freezer control electronics are implemented using non-ohmic coupling;
the non-ohmic coupling between the first freezer control electronics and the first box control electronics transfers operating power from the first freezer control electronics to the first box control electronics;

the non-ohmic coupling between the first box control electronics and the container electronics of each sample container transfers operating power from the box control electronics to the container electronics;
the first freezer further comprises a second-temperature side having a second temperature greater than the first temperature;
the first freezer control electronics is housed within the second-temperature side of the first freezer;
the first box control electronics is implemented on a printed circuit board within which is integrated each corresponding reader coil;
the system further comprises at least one first sample container;
the first sample container comprises (i) an untagged tube containing the sample and (ii) a tagged tube containing the container electronics, wherein the untagged tube is inserted within the tagged tube;
the tagged tube comprises a mechanism that engages structure of the untagged tube to retain the untagged tube within the tagged tube;
one of (1) the mechanism comprises an insert that cuts into structural material of the untagged tube to retain the untagged tube within the tagged tube and (2) the untagged tube comprises a ridge that engages with the mechanism to retain the untagged tube within the tagged tube; and
the untagged tube is configured to be released from the tagged tube by inserting a releasing tool between the structure of the untagged tube and the mechanism of the tagged tube.

27. A system for storing samples, the system comprising at least one first cabinet, at least one first box, and one or more sample containers, wherein:
the first cabinet comprises first cabinet control electronics and is configured to receive the first box;
the first box comprises first box control electronics and is configured to receive the one or more sample containers, each sample container comprising container electronics and configured to store a sample;
the first box control electronics is configured to communicate with the container electronics of each sample container received by the first box;
the container electronics of each sample container is configured to communicate sample-identification information for the sample stored in the sample container to the first box control electronics;
the first box control electronics is configured to communicate the sample-identification information towards the first cabinet control electronics;
the first cabinet control electronics is configured to communicate the sample-identification information to a host computer for the system;
the system further comprises at least one first sample container; and
the first sample container comprises (i) an untagged tube configured to contain the sample and (ii) a tagged tube containing the container electronics, wherein the untagged tube is inserted within the tagged tube.

28. The system of claim 27, wherein the tagged tube comprises a mechanism that engages structure of the untagged tube to retain the untagged tube within the tagged tube.

29. The system of claim 28, wherein the mechanism comprises an insert that cuts into structural material of the untagged tube to retain the untagged tube within the tagged tube.

30. The system of claim 28, wherein the untagged tube comprises a ridge that engages with the mechanism to retain the untagged tube within the tagged tube.

31. The system of claim 28, wherein the untagged tube is configured to be released from the tagged tube by inserting a releasing tool between the structure of the untagged tube and the mechanism of the tagged tube.

* * * * *